US008609389B2

(12) United States Patent
Harada et al.

(10) Patent No.: US 8,609,389 B2
(45) Date of Patent: Dec. 17, 2013

(54) MILK-CLOTTING PROTEASE DERIVED FROM A MICROORGANISM

(75) Inventors: Kazunori Harada, Hachioji (JP); Hiroyuki Kobayashi, Hachioji (JP); Taro Suga, Hachioji (JP); Hiroyuki Yamaguchi, Hachioji (JP); Akira Tsunoda, Hachioji (JP); Shigeaki Kato, Hachioji (JP)

(73) Assignee: Meito Sangyo Co., Ltd., Nagoya-shi, Aichi (JP)

( * ) Notice: Subject to any disclaimer, the term of this patent is extended or adjusted under 35 U.S.C. 154(b) by 264 days.

(21) Appl. No.: 13/257,066

(22) PCT Filed: Mar. 19, 2010

(86) PCT No.: PCT/JP2010/055485
§ 371 (c)(1),
(2), (4) Date: Oct. 28, 2011

(87) PCT Pub. No.: WO2010/110464
PCT Pub. Date: Sep. 30, 2010

(65) Prior Publication Data
US 2012/0040436 A1    Feb. 16, 2012

(30) Foreign Application Priority Data
Mar. 24, 2009    (JP) ................. 2009-071592

(51) Int. Cl.
*C12N 9/50* (2006.01)
*C12N 1/20* (2006.01)
*C12N 15/00* (2006.01)
*C07H 21/04* (2006.01)

(52) U.S. Cl.
USPC ............. 435/219; 435/252.3; 435/320.1; 536/23.2

(58) Field of Classification Search
USPC ........................................ 435/219
See application file for complete search history.

(56) References Cited

U.S. PATENT DOCUMENTS

2005/0064403 A1    3/2005   Edens et al.

FOREIGN PATENT DOCUMENTS

| EP | 0 536 770 | 4/1993 |
|---|---|---|
| JP | 2-018834 | 10/1983 |
| JP | 58-175487 | 10/1983 |
| RU | 2296160 C2 | 3/2007 |
| WO | WO 00/08196 A2 | 2/2000 |
| WO | WO 2005/075654 A1 | 8/2005 |

OTHER PUBLICATIONS

Database: GenBank: Accession No. AAB24375.1, May 8, 1993, 1 page.
Office Action issued Aug. 14, 2012 by the Russian Patent Office to corresponding Russian application No. 2011142793/10(060474).
Decision on Grant issued in Russian Patent Application No. 2011142793/10(064074) on May 16, 2013.
Aikawa et al., "Protein engineering of the milk-clotting aspartic Proteinases," *Scand J Clin Lab Invest*, vol. 52 (Suppl. 210), pp. 51-58 (1992).
Tonouchi et al., "Cloning and sequencing of a gene for *Mucor rennin*, an aspartate protease from *Mucor pusillus*," *Nucleic Acids Research*, vol. 14(19), pp. 7557-7568 (1986).
Office Action issued in Russian Patent Application No. 2011142793/10(064074), on Dec. 12, 2012.
Aikawa, et al. "Replacements of Amino Acid Residues at Subsites and Their Effects on the Catalytic Properties of *Rhizomucor pusillus* Pepsin, an Aspartic Proteinase from *Rhizomucor pusillus*," *Journal of Biochemistry*, vol. 129, No. 5, pp. 791-794, 2001.
Baudyš, et al. "Protein Chemical Characterization of *Mucor pusillus* Aspartic Proteinase," *FEBS Letters*, vol. 235, Nos. 1-2, pp. 271-274, 1988.
Park, et al. "Site-directed Mutagenesis of Conserved Trp39 in *Rhizomucor pusillus* Pepsin: Possible Role of Trp39 in Maintaining Tyr75 in the Correct Orientation for Maximizing Catalytic Activity," *Journal of Biochemistry*, vol. 121, No. 1, pp. 118-121, 1997.
Yang, et al. "Crystal Structure of the Aspartic Proteinase from *Rhizomucor miehei* at 2.15 Å Resolution," *Journal of Molecular Biology*, vol. 268, No. 2, pp. 449-459, 1997.
International Search Report dated Jul. 16, 2010 issued to international application No. PCT/JP2010/055485.
Written Opinion of the International Searching Authority dated Jul. 16, 2010 issued to international application No. PCT/JP2010/055485.

*Primary Examiner* — Tekchand Saidha
(74) *Attorney, Agent, or Firm* — Knobbe, Martens, Olson & Bear LLP

(57) ABSTRACT

The present invention provides an improved type protease which comprises an amino acid sequence that is at least 75% identical to SEQ ID NO:3, said improved type protease has at least one mutation selected from the group consisting of: (A) replacement of glutamine corresponding to glutamine at position 265 in SEQ ID NO: 3 with an acidic amino acid; and (B) replacement of glutamine at position 266 in SEQ ID NO: 3 with an acidic amino acid, and wherein said improved type protease has milk-clotting activity.

20 Claims, 2 Drawing Sheets

Fig. 2

```
RMPP    1    AEGDGSVDTPGLYDFDLEEYAIPVSIGTPGQDFYLLFDTGSSDTWVPHKGCDNSEGCVGK    60
             A  DGSVDTPG YDFDLEEYAIPVSIGTPGQDF LLFDTGSSDTWVPHKGC  SEGCVG
RMMP    1    AAADGSVDTPGYYDFDLEEYAIPVSIGTPGQDFLLLFDTGSSDTWVPHKGCTKSEGCVGS    60

RMPP   61    RFFDPSSSSTFKETDYNLNITYGTGGANGIYFRDSITVGGATVKQQTLAYVDNVSGPTAE   120
             RFFDPS+SSTFK T+YNLNITYGTGGANG+YF DSI +G  TV +Q LAYVDNV GPTAE
RMMP   61    RFFDPSTSSTFKATNYNLNITYGTGGANGLYFEDSIAIGDTTVTKQILAYVDNVRGPTAE   120

RMPP  121    QSPDSELFLDGIFGAAYPDNTAMEAEYGDTYNTVHVNLYKQGLISSPVFSVYMNTNDGGG   180
             QSP++++FLDG+FGAAYPDNTAMEAEYG TYNTVHVNLYKQGLISSP+FSVYMNTN G G
RMMP  121    QSPNADIFLDGLFGAAYPDNTAMEAEYGSTYNTVHVNLYKQGLISSPLFSVYMNTNSGTG   180

RMPP  181    QVVFGGVNNTLLGGDIQYTDVLKSRGGYFFWDAPVTGVKIDGSDAVSFDGAQAFTIDTGT   240
             +VVFGGVNNTLL GDI YTDV+   GGY+FWDAPVTG+ +DGS AV F  QAFTIDTGT
RMMP  181    EVVFGGVNNTLLSGDIAYTDVMSRYGGYYFWDAPVTGITVDGSAAVRFSRPQAFTIDTGT   240

RMPP  241    NFFIAPSSFAEKVVKAALPDATESQQGYTVPCSKYQDSKTTFSLVLQKSGSSSDTIDVSV   300
             NFFI PSS A K+VKAALPDATE+QQG+ VPC+ YQ+SK+T S+V+QKSGSSSDTI++SV
RMMP  241    NFFIMPSSAASKIVKAALPDATETQQGWVVPCASYQNSKSTISIVMQKSGSSSDTIEISV   300

RMPP  301    PISKMLLPVDKSGETCMFIVLPDGGNQFIVGNLFLRFFVNVYDFGKNRIGFAPLASGYEN   360
             P+SKMLLPVD+S ETCMFI+LPDGGNQ+IVGNLFLRFFV+VYDFG NRIGFAPLAS YEN
RMMP  301    PVSKMLLPVDQSNETCMFIILPDGGNQYIVGNLFLRFFVSVYDFGNNRIGFAPLASAYEN   360
```

MILK-CLOTTING PROTEASE DERIVED FROM A MICROORGANISM

CROSS-REFERENCE TO RELATED APPLICATIONS

This application is the U.S. National Phase under 35 U.S.C. §371 of International Application PCT/JP2010/055485, filed Mar. 19, 2010, which claims priority to JP Application No. 2009-071592, filed Mar. 24, 2009.

TECHNICAL FIELD

The present invention relates to a protease having improved milk-clotting activity derived from a microorganism. The protease is preferably used for the production of cheese.

BACKGROUND ART

Calf rennet has been used as a milk-clotting enzyme for the production of cheese for many years. A milk-clotting activity of the calf rennet is mostly attributed to chymosin, which is an acid protease and has site-specific protease activity for milk casein with low site-nonspecific activity (digest specifically the peptide bond between phenylalanine at position 105 and methionine at position 106 in the amino acid sequence of κ-casein). Nonspecific protease activity is thought to lead to reduction in yield of the production of cheese and to generation of a bitter-taste peptide during ripening. From this reason, chymosin is an excellent milk-clotting enzyme.

However, decreases in calf slaughter and increases of cheese demand have made it difficult to supply the calf rennet. Nowadays, a milk-clotting enzyme derived from microorganisms such as *Rhizomucor miehei* and *Rhizomucor pusillus*, and a recombinant chymosin produced by introducing a calf chymosin gene into fungi or yeast are widely used as a milk-clotting enzyme.

The above-mentioned milk-clotting enzyme derived from a microorganism, as compared with the calf chymosin or recombinant chymosin, has a higher nonspecific protease activity. It is a problem that C/P ratio (ratio of milk-clotting activity to protease activity) which is important as characteristics of the milk-clotting enzyme is low. In order to solve such a drawback, in *Rhizomucor pusillus*, a variant gene of the milk-clotting enzyme obtained by site-directed mutagenesis with genetic engineering has been expressed and evaluated. In the variant, C/P ratio was improved to be better than a wild type by replacing glutamic acid at position 19 with alanine in the amino acid sequence of the milk-clotting enzyme (Non-patent document 1).

However, since the milk-clotting activity of the variant milk-clotting enzyme decreases by about 40 percent with the amino acid replacement, it has been difficult to put such an enzyme into a practical application. Thus, a milk-clotting enzyme derived from a microorganism in which C/P ratio is high and the milk-clotting activity is maintained or improved has been desired.

Moreover, acylation of the milk-clotting enzyme derived from microorganisms such as *Rhizomucor pusillus* and *Rhizomucor miehei* with dicarboxylic anhydride in order to improve C/P ratio has been attempted (Patent document 1). With this method, some improvement was obtained; however, those are not yet satisfactory.

[Patent document 1] Japanese Patent No. 2-18834B
[Non-patent document 1] *J. Biochem.* 129, 791-794, 2001

SUMMARY OF THE INVENTION

An object of the present invention is to provide a protease suitable for milk clotting in which an activity (hereinafter also referred to as a "nonspecific protease activity") to digest a peptide bond other than the bond between phenylalanine at position 105 and methionine at position 106 in the amino acid sequence of κ-casein is low and a milk-clotting activity is maintained or improved.

The inventors of the present invention intensively studied for overcoming the above-described problem, and isolated, among mutant strains of microorganisms that produces a milk-clotting enzyme, a mutant strain that produces a milk-clotting enzyme whose C/P ratio is improved because of reduction in the nonspecific protease activity; isolated a gene of the improved type milk-clotting enzyme; determined the nucleotide sequence thereof; expressed the gene; and measured milk-clotting activity and C/P ratio of the improved type milk-clotting enzyme, thereby completed the present invention.

Accordingly, the present invention provides a protease derived from the microorganism having the milk-clotting activity, whose milk-clotting activity is maintained or increased and C/P ratio is increased, also provides a DNA coding for this protease, a vector containing the DNA and a transformed cell into which the vector has been introduced.

One aspect of the present invention is to provide an improved type protease which comprises an amino acid sequence that is at least 75% identical to SEQ ID NO: 3, said improved type protease has at least one mutation selected from the group consisting of:

(A) replacement of glutamine corresponding to glutamine at position 265 in SEQ ID NO: 3 with an acidic amino acid; and (B) replacement of glutamine at position 266 in SEQ ID NO: 3 with an acidic amino acid, and wherein said improved type protease has milk-clotting activity.

Another aspect of the present invention is to provide the improved type protease as described above, which is selected from the group consisting of:

(A) a protein comprising the amino acid sequence of SEQ ID NO:3 or 43 except that glutamine at position 265 and/or glutamine at position 266 is(are) replaced with an acidic amino acid;

(B) a protein comprising the amino acid sequence of SEQ ID NO:3 or 43 except that glutamine at position 265 and/or glutamine at position 266 is(are) replaced with an acidic amino acid and not more than 10 amino acids (preferably, not more than 5 amino acids, more preferably not more than 3 amino acids, furthermore preferably not more than 2 amino acids) at positions other than 265 and 266 are substituted, deleted, inserted or added, and wherein said improved type protease has milk-clotting activity.

Another aspect of the present invention is to provide the improved type protease as described above, wherein said acidic amino acid is glutamic acid or aspartic acid.

Another aspect of the present invention is to provide the improved type protease as described above, wherein glutamic acid at position 19 is replaced with valine, alanine, isoleucine or leucine.

Another aspect of the present invention is to provide the improved type protease as described above, wherein threonine at position 81 is replaced with glutamine or aspartic acid.

Still further aspect of the present invention is to provide a DNA coding for the improved type protease as described above.

Still further aspect of the present invention is to provide an expression vector comprising the DNA as described above.

Still further aspect of the present invention is to provide a transformed cell into which the expression vector as described above is introduced.

Still further aspect of the present invention is to provide the transformed cell as described above, said transformed cell being *Saccharomyces cerevisiae*.

Still further aspect of the present invention is to provide a method for producing an improved type protease having milk-clotting activity, comprising the steps of culturing the transformed cell as described above in a culture medium and collecting the improved type protease in the culture medium.

Since the milk-clotting activity is maintained or improved and C/P ratio is high, higher yield of cheese production with the improved type enzyme of the present invention is expected. Furthermore, higher C/P ratio implies generally that the development of bitter taste in cheese during ripening is reduced, i.e. high quality cheese can be manufactured with the improved enzyme.

BRIEF DESCRIPTION OF THE DRAWINGS

FIG. 2 shows the sequence alignment of the protease from *Rhizomucor pusillus* (RMPP) and the protease from *Rhizomucor miehei* (RMMP).

DESCRIPTION OF EMBODIMENTS OF THE INVENTION

Figure 1:
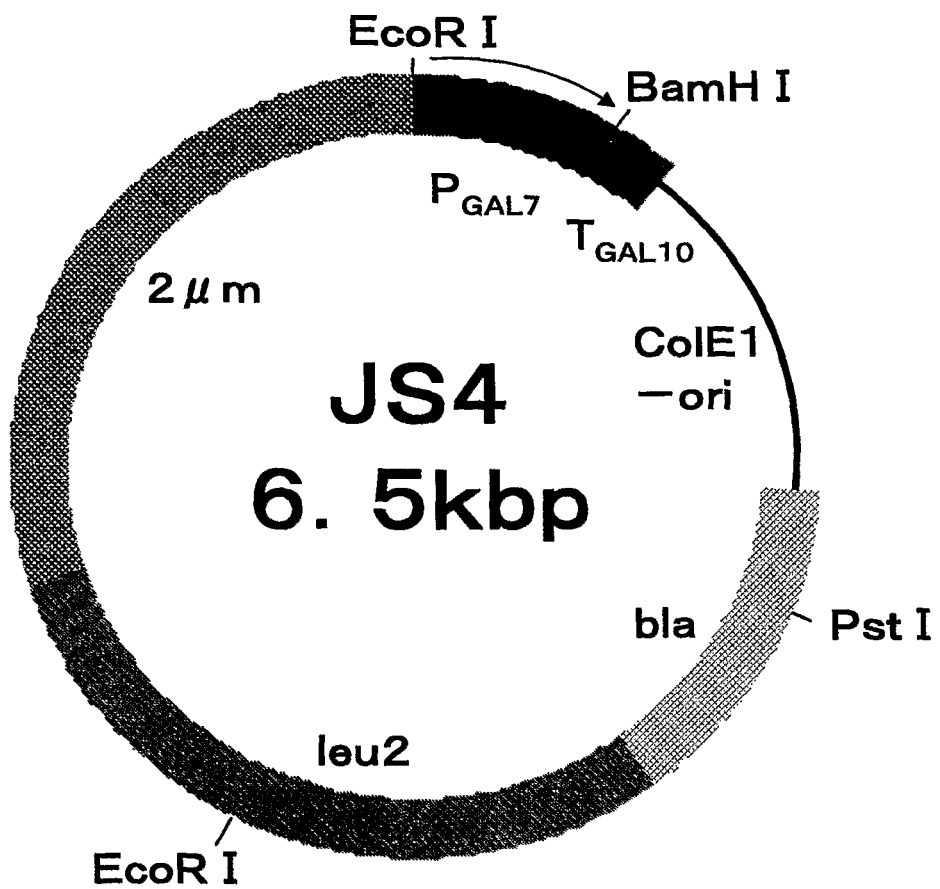
FIG. 1 shows the structure of an expression vector JS4.

The present invention will be illustrated in detail below.
1. The Improved Type Protease (Milk-Clotting Enzyme) of the Present Invention The improved type protease of the present invention comprises an amino acid sequence that is at least 75% identical to SEQ ID NO: 3, and has at least one mutation selected from the group consisting of:
(A) replacement of glutamine corresponding to glutamine at position 265 in SEQ ID NO: 3 with an acidic amino acid; and
(B) replacement of glutamine at position 266 in SEQ ID NO: 3 with an acidic amino acid, and has milk-clotting activity.

Examples of the above-mentioned acidic amino acid include glutamic acid and aspartic acid.

The improved type protease of the present invention preferably has sequence identity not less than 90%, more preferably not less than 95% to the whole amino acid sequence of SEQ ID NO: 3.

In one embodiment, the improved type protease of the present invention can be obtained by introducing the mutation(s) into a wild type protease derived from *Rhizomucor miehei* (SEQ ID NO:3). In this embodiment, the improved type protease of the present invention is selected from the group consisting of:
(A) a protein comprising the amino acid sequence of SEQ ID NO:3 except that glutamine at position 265 and/or glutamine at position 266 is(are) replaced with an acidic amino acid;
(B) a protein comprising the amino acid sequence of SEQ ID NO:3 except that glutamine at position 265 and/or glutamine at position 266 is(are) replaced with an acidic amino acid and not more than 10 amino acids at positions other than 265 and 266 are substituted, deleted, inserted or added, and has milk-clotting activity.

FIG. 2 shows the sequence alignment of the protease from *Rhizomucor pusillus* and the protease from *Rhizomucor miehei*. In both sequences, the amino acids at positions 265 and 266 are conserved, so the improved type protease of the present invention can also be obtained by introducing the mutation(s) into a wild type protease from *Rhizomucor pusillus* (SEQ ID NO: 43). That is, in another embodiment, the improved type protease of the present invention may be a protein comprising the amino acid sequence of SEQ ID NO: 43 except that glutamine at position 265 and/or glutamine at position 266 is(are) replaced with an acidic amino acid. Further, this improved type protease may have another mutation (substitutions, deletions, insertions, or additions of not more than 10 amino acids) other than replacement(s) in glutamine at position 265 and/or glutamine at position 266 as long as it has milk-clotting activity.

In the improved type protease of the present invention, glutamic acid at position 19 and threonine at position 81 in the amino acid sequence of SEQ ID NO:3 or 43 may be replaced with other amino acids. Glutamic acid at position 19 is preferably replaced with valine, alanine, isoleucine or leucine, whereas threonine at position 81 is preferably replaced with glutamine or aspartic acid.

In the present invention, "position 265", "position 266", "position 19" and "position 81" do not necessarily indicate an absolute position from the N-terminal of the protease but indicate a relative position with compared to the amino acid sequence of SEQ ID NO:3 or 43. For instance, in the protease having the amino acid sequence of SEQ ID NO:3 or 43, when deletion of one amino acid happens at a position N-terminal side from position 265, the above-mentioned position 265 is then to be position 264. Even in such a case, the amino acid at position 264 counted from N-terminal residue is the amino acid of "position 265" in the present invention. The absolute position of the amino acid is determined by alignment of the amino acid sequence of a protease of interest with the amino acid sequence of SEQ ID NO:3 or 43. The amino acid indicated by the term "corresponding to" also means an amino acid at a relative position with compared to the amino acid sequence of SEQ ID NO:3 or 43.

SEQ ID NO: 3 and SEQ ID NO:43 are amino acid sequence of the mature type protease. The improved type protease of the present invention may include the amino acid sequence of a signal peptide, propeptide and the like.

With the method as described in the Examples of this description, by breeding a mutant strain that produces an improved type protease with high C/P ratio from a microorganism that produces a wild type protease having the milk-clotting activity with comparatively low C/P ratio and culturing the mutant strain in a medium, the improved type protease of the present invention can be obtained from the cell of the mutant strain or from the medium. Examples of the microorganism that produces the wild type protease with the comparatively low C/P ratio include a wild type strain of *Rhizomucor miehei* (ATCC16457), *Rhizomucor pusillus* (ATCC16458), and derivative strains thereof. These strains can be purchased from American Type Culture Collection (ATCC; P.O. Box 1549 Manassas, Va. 20108 USA). The improved type protease of the present invention can also be obtained by isolating a DNA coding for the improved type protease from the above-mentioned mutant strain and expressing the DNA.

In addition, the improved type protease of the present invention can also be obtained by isolating a DNA coding for the amino acid sequence of SEQ ID NO:3 or 43 from the wild type strain of *Rhizomucor miehei* (ATCC16457), *Rhizomucor pusillus* (ATCC16458), or derivative strains thereof and modifying the DNA with site-directed mutagenesis so as to encode the improved type protease of the present invention, followed by expressing the modified DNA.

The expression of the above-mentioned DNA can be carried out by constructing an expression vector containing the above-mentioned DNA and introducing it into a host cell. Although the host cell may be a prokaryotic cell or eukaryotic cell, a eukaryotic cell is preferable. Examples of the eukaryotic cell include yeast cell, a fungus cell, and a plant cell. Yeast cell is preferable and *Saccharomyces cerevisiae* cell being particularly preferred.

Moreover, the expression of the above-mentioned DNA can also be carried out in a cell-free system.

C/P ratio of the improved type protease of the present invention is higher than C/P ratio of a corresponding wild type protease (SEQ ID NO:3 or 43). C/P ratio of the improved type protease of the present invention is preferably not less than 1.2 times, more preferably not less than 1.5 times, further more preferably not less than 2.0 times as high as C/P ratio of the wild type protease (SEQ ID NO:3 or 43).

C/P ratio herein indicates [milk-clotting activity (MCA)]/[protease activity (PA)]. Measurement of PA and MCA can be carried out with the following methods. As for the measurement of MCA, although there is the International Standard Method (described in ISO15174, IDF176; first edition 2002-09-01, Self-imposed Specifications for Food Additives), a value of MCA in the present description is calculated by the following method (herein, referred to as Meito method).

[1] Measurement of PA

Casein made from milk (manufactured by Wako Pure Chemical Industries, Ltd.) is dissolved in a 0.05 M disodium hydrogen phosphate solution and adjusted to pH 6.0 with 1 mol/l hydrochloric acid test solution, to prepare a 0.6% casein substrate solution. A test sample (0.2 ml), which is diluted appropriately, is added to 1 ml of this substrate solution. The mixture is allowed to react at 37° C. for 10 to 30 minutes and then the reaction is terminated by adding 1 ml of a reaction stop solution (a mixed solution of 0.11 mol/l trichloroacetic acid, 0.21 mol/l anhydrous sodium acetate, and 0.33 mol/l acetic acid). Supernatant is obtained by centrifugation, and 1 ml of 0.55 mol/l anhydrous sodium carbonate is added to 0.4 ml of the supernatant, and then 0.2 ml of a phenol reagent manufactured by Wako Pure Chemical Industries, Ltd. (Folin-Ciocalteu reagent) diluted two-fold is added. The mixture is allowed to react for at 37° C. for 30 minutes and then absorbance (optical path length: 1 cm) is measured at 660 nm. Separately, 1 ml of the reaction stop solution is added to 1 ml of the substrate solution, followed by addition of 0.2 ml of a test sample. Thereafter, the mixture is prepared in the same procedures and the resultant is used as a blank. A value obtained by subtracting the absorbance of the blank from the absorbance of the test sample is converted into the amount of free tyrosine to calculate a value of PA. The unit of PA is Unit/ml. This 1 Unit refers to the amount of enzyme which brings about an increase in the phenol reagent coloration substance equivalent to 1 mol of tyrosine in 1 minute in the above-mentioned method. Also, the correlation equation of the tyrosine and phenol reagent coloration substance is obtained by preparing a tyrosine calibration curve as described below.

Tyrosine Calibration Curve

A standard tyrosine (molecular weight 181.2, manufactured by Wako Pure Chemical Industries, Ltd.) is dried at 105° C. for 3 hours. Then 0.050 g of the standard is precisely weighed and dissolved in 0.2 mol/l hydrochloric acid test solution to exactly attain a final volume of 50 ml. 1, 2, 3 and 4 ml of this solution are precisely measured and 0.2 mol/l hydrochloric acid test solution is added to each to exactly attain a volume of 100 ml. Two ml of each solution is precisely measured. Then, 5 ml of 0.55 mol/l sodium carbonate test solution and 1 ml of the phenol reagent diluted two folds are added. Immediately after that, the mixture is mixed with shaking and allowed to stand at 37±0.5° C. for 30 minutes. From the obtained solution, just 2 ml of the obtained solution is taken and absorbance A1, A2, A3, and A4 at the wavelength of 660 nm are measured together with a control solution prepared in a similar manner. By taking the absorbance A1, A2, A3, and A4 along a vertical axis and the amount of tyrosine (μmol) in 2 ml of each solution along a horizontal axis, the calibration curve is prepared to determine the amount of tyrosine (μmol) for an absorbance difference of 1.

[2] Assay Method for MCA (Meito Method)

Nonfat dry milk, preferably manufactured by CHR.HANSEN, is dissolved (10%) in 0.01 M calcium chloride (pH 6.0) to be used as a substrate. A test sample solution (0.5 ml) prepared to a concentration at which curd fragments are formed for 2 to 5 minutes, preferably in 2 minutes and 30 seconds, is added to 5 ml of this substrate, and the mixture is kept at 35° C. While agitating the mixture with a glass rod, the curd fragment formation is observed to measure time for the formation. Compared with a value of the standard whose MCA is known, which value is measured similarly, MCA is determined by calculating how much (fold-wise) more amount of substrate a unit amount of the test sample can clot the substrate in a unit time. The calculation equation is as follows:

$$MCA\ (Mu/ml) = S \times (T_S \times W_S)/(T \times W)$$

S: specific activity of milk-clotting enzyme of the standard (Mu/g)

$T_S$: time for milk clotting of the standard solution (second)

$W_S$: amount of the standard in 1 ml of the standard solution (g)

T: time for milk clotting of the test sample solution (second)

W: amount of the test sample in 1 ml of the test sample solution (ml)

In addition, MCA can also be calculated per unit protein amount by quantifying the total amount of proteins contained in the test sample. In Example 13 described later, MCA is calculated per 1 mg of protein (Mu/mg protein).

The value of MCA calculated by the above-mentioned method has correlation with the value of MCA calculated by the International Standard (described in ISO15174, IDF176; first edtion 2002-09-01, Self-imposed Specifications for Food Additives). The correlation can be shown by the following formula.

1 international standard unit (IMCU/ml)≈1 Meito method unit (Mu/ml)/100

MCA of the protease of the present invention is preferably substantially equal to or higher than MCA of the wild type protease. When the protease of the present invention and the wild type protease (SEQ ID NO:3 or 43) are prepared under the identical condition to compare MCA, MCA of the improved type protease of the present invention is preferably not less than 0.8 times, more preferably not less than 0.9 times, further more preferably not less than 1.0 time as high as MCA of the wild type protease.

An example of preparation of the improved type protease of the present invention and the wild type protease under the identical condition includes incorporating DNA coding for each protease in an identical vector for gene expression, introducing each of this expression vector into a cell of an identical strain in an identical condition, and culturing the cell under an identical culture condition to obtain a culture as a protease solution. The obtained culture may be condensed in an identical manner or purified in an identical manner for use.

2. DNA Coding for the Improved Type Protease of the Present Invention

The DNA of the present invention is DNA coding for the improved type protease of the present invention. Specific examples of the DNA of the present invention include a DNA comprising nucleotides 208 to 1290 in SEQ ID NO:1 and a DNA comprising a sequence that hybridizes with the nucleotide sequence complementary to nucleotides 208 to 1290 in SEQ ID NO:1 under stringent conditions; and coding for the improved type protease having the above-described properties. Specific examples of the DNA of the present invention also include a DNA comprising the nucleotide sequence of SEQ ID NO:42 and a DNA comprising a sequence that hybridizes with the nucleotide sequence complementary to the nucleotide sequence of SEQ ID NO:42 under stringent conditions; and coding for the improved type protease having the above-described properties. Stringent conditions mean conditions in which a so-called specific hybrid is formed while a nonspecific hybrid is not formed. Although the conditions vary depending on the nucleotide sequence or its length, examples thereof include conditions in which DNA with high homology, for example, DNAs having a homology of not less than 75%, preferably not less than 90%, further preferably not less than 95%, mutually hybridize, and DNAs having a homology with lower than that do not hybridize, or conditions of hybridization, which is a usual condition for washing in Southern hybridization, at 60° C. and 1×SSC, 0.1% SDS, preferably 0.1×SSC and a salt concentration equivalent to 0.1% SDS.

DNA coding for the protease of the present invention can be isolated from the mutant strain having the above-mentioned improved type protease by conventional gene cloning method. For instance, it can be isolated by selecting the DNA from a gene library of the above-mentioned mutant strain by hybridization with a synthetic oligonucleotide probe based on the nucleotide sequence of SEQ ID NO:1 or 42.

Also, DNA coding for the improved type protease of the present invention can be obtained by designing primers based on the nucleotide sequence of known genome DNA or cDNA of the wild type protease gene, and amplifying the DNA from genomic DNA and cDNA library of the above-mentioned mutant strain using the primers.

DNA obtained by introducing a site-directed mutation into a wild type DNA is also included in DNA coding for the protease of the present invention.

For example, a DNA coding for the improved type protease of the present invention can be readily obtained by isolating a DNA coding for the amino acid sequence of SEQ ID NO:3 from *Rhizomucor miehei* wild type strain (ATCC16457) or its derivative strain, and introducing the site-directed mutation into it. A DNA coding for the improved type protease of the present invention can be also obtained by isolating a DNA coding for the amino acid sequence of SEQ ID NO:43 from *Rhizomucor pusillus* wild type strain (ATCC16458) or its derivative strain, and introducing the site-directed mutation into it.

Introduction of the site-directed mutation can be carried out by a method known to those skilled in the art. For instance, mutations can be introduced by synthesizing primers having a restriction enzyme cleavage site at one end and containing the mutation site at the other end, and replacing a corresponding portion in an unmutated gene with the mutated portion (cassette mutation method).

As the method for introducing the site-directed mutation, for example, Gapped duplex method and kunkel method are known. The kunkel method is based on a principle in which the unmutated gene is cloned into a single-stranded phage; and a complementary strand is synthesized using synthetic DNA containing a mismatch to a mutated point as a primer; and then a new phage and replicated DNA are made with only the obtained complementary strand containing the mutation as a template. The site-directed mutagenesis can be carried out using a commercially available kit.

3. Expression Vector of the Present Invention

The expression vector of the present invention is used for expressing the improved type protease of the present invention. It can have a structure in which a promoter sequence that controls the expression of the DNA is linked upstream of the DNA coding for the improved type protease of the present invention. Furthermore, a terminator can also be linked downstream of the DNA.

As the above-mentioned promoter, when a host is *E. coli*, trp, lac, taq, $\lambda P_L$ or the like can be used. When a host is yeast, a promoter of GAL7, ADH, TPI or PHO5 or the like is preferred, and among those, GAL7 is preferred because it strongly promotes gene expression (Nogi Y. et al. *Nucl. Acids Res.* 11, 8555-8568 (1983)).

Examples of the terminator include TPI, GAPDH, and GAL10. By linking the above-mentioned promoter, DNA coding for the improved type protease of the present invention, the above-mentioned terminator in the order from the 5' upstream to 3' downstream and inserting the resultant into a vector, the expression vector of the present invention can be constructed.

As a vector capable of replicating in yeast, any type of the plasmid of so-called YIp, YRp, YEp and YCp can be used. From the viewpoint of the copy number and stability, the YEp type is preferred. Since these plasmids generally contain an unnecessary sequence, in consideration of the stability of the plasmid, or in order to facilitate modification of the plasmid, it is preferred to delete the unnecessary sequence.

A selection marker gene for selecting a recombinant or a reporter gene for checking the expression of the introduced gene can also be inserted in the expression vector of the present invention. Examples of the selection marker gene include hygromycin resistance genes, kanamycin resistant genes, and ampicillin resistance genes. Examples of the reporter gene include beta-glucuronidase (GUS) genes, chloramphenicol acetyltransferase (CAT) genes, luciferase (LUC) genes and GFP genes. Moreover, in order to express the improved type protease of the present invention as a secretory type or to facilitate purification of the protease expressed, an additional sequence may be included in the expression vector of the present invention. In this case, the protease of the present invention is expressed as a fusion protein with a protein or peptide encoded by the additional sequence. Examples of the additional sequence include a nucleotide sequence coding for a signal peptide or propeptide and nucleotide sequence coding for a His-tag, or GST-tag.

4. Transformed Cell of the Present Invention

A transformed cell of the present invention is a cell into which the expression vector of the present invention has been introduced, the cell being capable of producing the improved type protease of the present invention. Although the cell may be a prokaryotic cell or may be a eukaryotic cell, it is preferred to be the eukaryotic cell.

Examples of the eukaryotic cell include yeast cell, fungus cell and, plant cell. Yeast cell is preferred and *Saccharomyces cerevisiae* being particularly preferred.

Examples of *Saccharomyces cerevisiae* include strains of SHY3, D13-1A and MC16.

A method for introducing the expression vector into the host cell can be appropriately selected depending on the types of host cell. Such methods are known to those skilled in the art. A transformant of *Saccharomyces cerevisiae*, for example, can be obtained by the following method.

*Saccharomyces cerevisiae* cultivated in YPD culture medium (1% yeast extract (manufactured by Difco), 2% Bactopeptone (manufactured by Difco) and 2% glucose) overnight is inoculated to a final volume of 10% into a fresh YPD culture medium, and cultured at 30° C. for 4 hours. The obtained culture (1.5 ml) is subjected to light centrifugation with a desk-top centrifuge to harvest cells. The cells are rinsed with 0.2 M LiSCN (manufactured by Kanto Chemical Co., Inc.) and suspended in 0.02 ml of 1 M LiSCN.

Subsequently, 0.01 ml of a solution containing the expression vector (about 1 to 10 μg) and 0.03 ml of 70% PEG4000 are mixed, and the mixture was kept at 30° C. for 1 hour. This mixture was diluted by adding 0.14 ml of sterilized water and then plated onto two SDah plates (0.67% Bacto-yeast nitrogen base w/o amino acid, 2% glucose, 0.002% adenine sulfate, 0.002% L-histidine-HCl, 2% agar). After incubated at 30° C. for 2 to 3 days, the transformant can be obtained.

5. Method for Producing the Improved Type Protease Having the Milk-Clotting Activity of the Present Invention By culturing the transformed cell of the present invention, the improved type protease of the present invention can be produced, and by expressing the improved type protease of the present invention as a fusion protein with a signal peptide for secretion, the improved type protease of the present invention can be accumulated in a medium. When an inducible promoter is used, induction is preferably carried out during culture. Although a method for culturing the transformed cell varies depending on the types of cell, conventional methods can employed.

An example of the method for culturing the transformant of *Saccharomyces cerevisiae* will be described below.

The transformant is cultured with shaking at 30° C. for two days in the 50 ml of YPD culture medium in a 500 ml Sakaguchi flask to proliferate yeast cells. The culture medium is centrifuged at 1000×g for 5 minutes to collect the cells. The cells are again suspended in 100 ml of YPGa1 culture medium (1% yeast extract, 2% Bactopeptone, 4% galactose (manufactured by Wako Pure Chemical Industries, Ltd.)), and cultured with shaking in a 500 ml Sakaguchi flask at 30° C. for three days.

The protease having the milk-clotting activity, which protease is secreted in the medium, can be used as it is in the state of existing in culture supernatant and can also be used by condensing the culture supernatant. The protease having the milk-clotting activity, which protease is secreted in the medium, may be purified or partially purified. Using a general method for purifying a protein, purification or partial purification can be carried out. For example, a technique including chromatography such as ion exchange or gel filtration, salting out with ammonium sulfate or sedimentation with an organic solvent can be used.

The purified enzyme can also be condensed by lyophilization, ultrafiltration membrane, sedimentation with the organic solvent or the like.

EXAMPLES

Hereinafter, the present invention will now be described concretely by way of Examples but the technical scope of the present invention is not restricted to these exemplified illustrations. Also, all gene manipulations can be carried out as described in *Molecular Cloning* (Cold Spring Harbor Laboratory Press (1989)).

Example 1

Acquisition of *Rhizomucor Miehei* Mutant Strain that Produces a Protease with Improved C/P Ratio A *Rhizomucor miehei* parent strain (CBS 182-67 (a derivative strain of ATCC16457)) that produces a protease was subjected to a mutagenesis treatment, thereby a mutant strain that secrets a protease with improved C/P ratio was obtained. The details are illustrated below.

(1) Mutagenesis Treatment

*Rhizomucor miehei* parent strain was grown on a malt plate (2% malt extract, 2% glucose, 0.1% peptone, 2% agar), and kept for 3 days to 1 week at 37° C. to allow spore formation. These spores were suspended in sterilized water using a glass spreader.

Nitrosoguanidine (N-methyl-N'-nitro-N-nitrosoguanidine, manufactured by SIGMA CHEMICAL CO.) was added to this spore suspension to a final concentration of 200 μg/ml. The mixture was treated at room temperature for 5 to 20 minutes such that the mortality rate is 90%. An appropriate amount of this mixture was plated on the malt plate, and the resulting plate was kept at 37° C. On the next day, each cluster of minute fungal hyphae obtained was inoculated in 8 ml of YPD culture medium (1% yeast extract, 2% peptone, 2% glucose), and culture supernatant after culturing at 37° C. for 4 days was used as a sample for measuring the protease activity (PA) and milk-clotting activity (MCA). The cells were stored at −80° C.

(2) Search for Improved Type Protease

As a result of measuring MCA and PA by the method described above, an improved type protease whose PA was much less than that of the parent strain and whose C/P ratio (MCA/PA) was greatly increased by 4.6 times as compared with the parent strain was obtained.

Example 2

Isolation of a Protease Gene from the Mutant Strain (1) Acquisition of the Chromosomal DNA of the Mutant Strain and the Parent Strain The mutant strain obtained in the Example 1 and the parent strain were grown on the malt plate, and kept at 37° C. for three days to one week to allow spore formation. These spores were suspended to sterilized water using a glass spreader. This spore suspension was seeded in 200 ml of YPD liquid medium in a 500 ml Sakaguchi flask such that about $1 \times 10^8$ spores were contained in each flask, and cultivated for two days at 37° C. At the time when the cells formed a pellet with a size of about 0.5 to 2 mm, the medium was filtered to remove excessive moisture and thus a wet weight of about 5 g of the cells was obtained.

After frozen with liquid nitrogen, the cells were transferred to a precooled mortar and 3 g of sea sand (850 to 1400 μm) was added. The mixture was ground finely to powder with a pestle under cooling with liquid nitrogen. This was suspended in 15 ml of a solution containing 0.05 M EDTA pH 8.5 and 0.2% SDS, which solution was preheated at 68° C., and the resultant was kept at 68° C. for 15 minutes. Then, it was left to stand and allowed to cool to room temperature, and cloudy supernatant was collected by centrifugation. After adding 1/10 volume of 3 M sodium acetate to the collected solution, the mixture was stirred mildly and supernatant was collected by centrifugation. Next, when 15 ml of isopropanol was added to the collected supernatant and mixed quietly, a lump of the genomic DNA and proteins appeared. After the generated precipitate was rinsed with 70% ethanol, the resultant was dried under reduced pressure, dissolved in 400 µl of TE, and 10 of RNase solution (10 mg/ml). The mixture was kept at 37° C. for 1 hour. After the end of the RNase treatment, a phenol/chloroform treatment and chloroform treatment were carried out, followed by ethanol precipitation, thereby the genomic DNA was obtained.

(2) Isolation of the Protease Gene from the Chromosomal DNA of the Mutant Strain and Parent Strain The protease gene was isolated by PCR using the chromosomal DNA derived from the mutant strain obtained above and the parent strain as a template. Based on the sequence of the protease of *Rhizomucor miehei* registered in the gene bank (DDBJ access number: E01264), primers of SEQ ID NO:5 and SEQ ID NO:6 were prepared. PCR condition was (a) at 94° C. for 2 minutes; (b) 28 cycles of 94° C. for 30 seconds-55° C. for 30 seconds-72° C. for 3 minutes; and (c) 72° C. for 5 minutes. As a polymerase, TaKaRa Ex Taq (manufactured by Takara Bio Inc.) was used. As a thermal cycler, TaKaRa PCR Thermal Cycler Dice Gradient (manufactured by Takara Bio Inc.) was used. As a result of determining the nucleotide sequence of the DNA fragment obtained by PCR, it was revealed that the amino acid sequence encoded by the DNA amplified with the chromosomal DNA of the parent strain as the template contained the amino acid sequence of SEQ ID NO:3. The amino acid sequence encoded by the DNA amplified with the chromosomal DNA of the mutant strain as the template contained the amino acid sequence of SEQ ID NO: 4 whereby the amino acid at position 19 was replaced with valine and the amino acid at position 266 was replaced with glutamic acid.

Hereinafter, the protease derived from the parent strain of *Rhizomucor miehei* is called wild type RMMP, and the improved type protease is called "improved RMMP" and a gene encoding the improved type protease is called "improved RMMP gene".

Example 3

Construction of a Plasmid Vector JS4 to Express a Foreign Protein Using Budding Yeast (*Saccharomyces cerevisiae*) MC16 as a Host.

JS5 (described in Japanese Patent No. 3012377 [0109]) was used as a starting material for constructing the plasmid vector JS4.

First, PCR was carried out using primer DNA of SEQ ID NOs:7 and 8 with JS5 as a template, thereby the PCR product of 0.55 kbp containing a GAL7 promoter region was obtained. PCR condition was at (a) 94° C. for 2 minutes; (b) 30 cycles of 98° C. for 10 seconds-52° C. for 30 seconds-72° C. for 1 minute; and (c) 72° C. for 5 minutes. As a polymerase, TaKaRa Ex Taq (manufactured by Takara Bio Inc.) was used. As a thermal cycler, TaKaRa PCR Thermal Cycler Dice Gradient (manufactured by Takara Bio Inc.) was used.

Next, the obtained PCR product was digested with restriction enzymes EcoR I and BamH I and inserted into pUC18 which was also digested with EcoR I and BamH I. The obtained plasmid was introduced into *E. coli* DH5α, and cells were spread on a LB agar plate containing 100 µg/ml ampicillin, 0.1 mM IPTG and 0.04 mg/ml X-GAL, and incubated at 37° C. for 16 hours. The appeared white colony was cultured with shaking in LB liquid medium containing 100 µg/ml ampicillin at 37° C. for 14 to 16 hours. From the transformant collected by centrifugation, the plasmid was extracted using QIAprep Miniprep kit (QIAGEN, hereinafter all plasmid extraction was carried out using this kit). For the inserted fragment, sequencing was carried out to confirm that unwanted mutations were not introduced.

Subsequently, the plasmid containing the insert fragment was digested with EcoR I and BamH I to obtain a DNA fragment of 0.55 kbp, and then this DNA fragment and the DNA fragment of about 6 kbp obtained by digesting JS5 with BamH I followed by partially digesting with EcoR I were ligated. The resultant plasmid was introduced into *E. coli* DH5α and the transformed *E. coli* was cultured on LB agar medium containing 100 µg/ml ampicillin at 37° C. for 16 hours. The appeared colony was cultured with shaking in the same liquid medium at 37° C. for 14 to 16 hours and then, from the transformant collected by centrifugation, the plasmid was extracted. This plasmid was digested with restriction enzymes EcoR I, BamH I, and Pst I, to confirm a migration pattern by agarose gel electrophoresis analysis. In this way, the expression vector JS4 was prepared.

As a starting material for constructing this plasmid vector, besides JS5, for example, JS52 (accession number FERM BP-3898) described in paragraph 0112 of Japanese Patent No. 3012377, can also be used.

Example 4

Construction of the Plasmid Vector for Expressing the Wild Type RMMP Gene and the Improved RMMP Gene Using primers (SEQ ID NOs:9 and 10) designed so as to have a BamH I site at the both termini of the nucleotide sequence containing DNA coding for wild type RMMP or improved RMMP having the Glu19Val/Gln266Glu mutations, which was obtained in Example 2, PCR was carried out. The obtained PCR product was digested with BamH I, inserted into JS4 which was similarly digested with BamHI and dephosphorylated, and the obtained vector was introduced into *E. coli* DH5α.

Using a forward primer that can anneal to the GALT promoter and a reverse primer that can anneal to the 3' terminus of the RMMP gene (SEQ ID NOs:11 and 10), colony-direct PCR was carried out. An *E. coli* transformant having the plasmid vector which was confirmed that a direction of the inserted gene was correct was subjected to liquid culture as described above. The plasmid was extracted and subjected to sequencing to confirm that unwanted errors were not introduced, thereby the plasmid vectors for expressing the wild type RMMP gene and improved RMMP gene were obtained.

Example 5

Construction of the Expression Vector of the Improved RMMP Genes in which the Site Directed Mutation is Introduced (I)

The PCR product of the wild type RMMP gene obtained by the method described in the Example 4, which contains a prepro sequence and the BamH I sites at each terminus, was digested with BamH I and inserted into pUC18 which was similarly digested with BamH I and dephosphorylated. The resultant plasmid was introduced into *E. coli* DH5α and then the plasmid was extracted from the obtained transformant and its nucleotide sequence was confirmed and thereby pRMMP-wt was obtained.

Next, by performing PCR using pRMMP-wt as a template, primer pairs of SEQ ID NOs:12 and 13, SEQ ID NOs:14 and 15, SEQ ID NOs:16 and 17, SEQ ID NOs:18 and 19, SEQ ID NOs:20 and 21, SEQ ID NO:22 and 23, or SEQ ID NOs:24 and 25 and PrimeSTAR Mutagenesis Basal Kit (Takara Bio Inc., hereinafter referred to as a "kit" for short), mutations were introduced such that one residue of either glutamic acid at position 19 or glutamine at position 266 in SEQ ID NO:3 was replaced with another amino acid. Design of primers to introduce the mutation and PCR were carried out referring to the manual appended to this kit. The mutagenesis experiments were carried out in accordance with the manual.

The obtained PCR products were introduced into *E. coli* DH5α, and cells were spread on a LB agar plate containing 100 μg/ml ampicillin, and incubated at 37° C. for 16 hours, thereby transformants were obtained. From these transformants, plasmids were extracted by the same method as described above and subjected to sequencing to confirm that unwanted mutations were not introduced.

By such procedures, genes coding for the improved RMMPs having mutation of Glu19Val, Glu19Ala, Glu19Ile, Glu19Leu, Glu19Phe, Gln266Glu or Gln266Asp were prepared. These plasmid vectors containing the improved RMMP gene were respectively termed as, pRMMP-E19V, pRMMP-E19A, pRMMP-E19I, pRMMP-E19L, pRMMP-E19F, pRMMP-Q266E and pRMMP-Q266D.

Further, using pRMMP-Q266E or pRMMP-Q266D as a template, primer pairs of SEQ ID NOs:12 and 13, SEQ ID NOs:14 and 15, SEQ ID NOs:16 and 17 or SEQ ID NOs:18 and 19 as well as the above-mentioned kit, PCR was carried out. The obtained PCR products were introduced into *E. coli* DH5α and then the plasmids were extracted from the obtained transformants in the same manner as described above and sequenced, thereby the genes coding for the improved RMMP having mutations of Glu19Val/Gln266Asp, Glu19Ala/Gln266Glu, Glu19Ala/Gln266Asp, Glu19Ile/Gln266Glu, Glu19Ile/Gln266Asp, or Glu19Leu/Gln266Glu were obtained. These plasmid vectors containing the improved RMMP gene were respectively termed as pRMMP-E19VQ266D, pRMMP-E19AQ266E, pRMMP-E19AQ266D, pRMMP-E19IQ266E, pRMMP-E19IQ266D, and pRMMP-E19LQ266E.

The thus obtained plasmid vectors were digested with BamH I, the obtained fragments were inserted into the JS4 by the method described above, thereby the expression vectors for each of the above-mentioned improved RMMP genes were obtained.

Example 6

Construction of the Expression Vector of the Improved RMMP Genes in which the Site Directed Mutation is Introduced (II)

Further, using pRMMP-wt as a template, using primer pairs of SEQ ID NOs:26 and 27, SEQ ID NOs:28 and 29, SEQ ID NOs:30 and 31, SEQ ID NOs:32 and 33, SEQ ID NOs:34 and 35 or SEQ ID NOs:36 and 37 as well as the above-mentioned kit, PCR was carried out. The obtained PCR products were introduced into *E. coli* DH5α and then the plasmids were extracted from the obtained transformants in the same manner as described above and sequenced, thereby the genes coding for improved RMMP having mutations of Gln265Glu, Gln265Asp, Gln265Glu/Gln266Glu, Gln265Glu/Gln266Asp, Gln265Asp/Gln266Glu or Gln265Asp/Gln266Asp were obtained. These plasmid vectors containing the improved RMMP gene were respectively termed as pRMMP-Q265E, pRMMP-Q265D, pRMMP-Q265EQ266E, pRMMP-Q265EQ266D, pRMMP-Q265DQ266E and pRMMP-Q265DQ266D.

The improved RMMP genes were obtained by digesting the thus obtained plasmid vector with BamH I and inserted into the JS4 by the method described above, thereby the expression vectors of the above-mentioned improved RMMP genes were obtained.

Example 7

Construction of the Expression Vectors of the Improved RMMP Genes in which the Site Directed Mutation is Introduced (III)

Using pRMMP-E19V, pRMMP-E19A or pRMMP-E19I as a template, primer pairs of SEQ ID NOs:30 and 31, SEQ ID NOs:32 and 33, SEQ ID NOs:34 and 35, or SEQ ID NOs:36 and 37 as well as the above-mentioned kit, PCR was carried out. The obtained PCR products were introduced into *E. coli* DH5α and then the plasmids were extracted from each of the obtained transformants in the same manner as described above and sequenced, thereby the genes coding for improved RMMP having mutations of Glu19Val/Gln265Glu/Gln266Glu, Glu19Val/Gln265Glu/Gln266Asp, Glu19Val/Gln265Asp/Gln266Glu, Glu19Val/Gln265Asp/Gln266Asp, Glu19Ala/Gln265Glu/Gln266Glu, Glu19Ala/Gln265Glu/Gln266Asp, Glu19Ala/Gln265Asp/Gln266Glu, Glu19Ala/Gln265Asp/Gln266Asp, Glu19Ile/Gln265Glu/Gln266Glu, Glu19Ile/Gln265Glu/Gln266Asp, Glu19Ile/Gln265Asp/Gln266Glu or Glu19Ile/Gln265Asp/Gln266Asp were obtained. These plasmid vectors containing the improved RMMP genes were respectively termed as pRMMP-E19VQ265EQ266E, pRMMP-E19VQ265EQ266D, pRMMP-E19VQ265DQ266E, pRMMP-E19VQ265DQ266D, pRMMP-E19AQ265EQ266E, pRMMP-E19AQ265EQ266D, pRMMP-E19AQ265DQ266E, pRMMP-E19AQ265DQ266D, pRMMP-E19IQ265EQ266E, pRMMP-E19IQ265EQ266D, pRMMP-E19IQ265DQ266E and pRMMP-E19IQ265DQ266D.

The improved RMMP genes were obtained by digesting the thus obtained plasmid vectors with BamH I and inserted into the JS4 by the method described above, thereby the expression vectors of the above-mentioned improved RMMP genes were obtained.

Example 8

Transformation of Budding Yeast MC 16 with the Expression Vector Containing Wild Type or Improved RMMP Gene The expression vectors produced as described above were introduced into the budding yeast MC16 (MATα, leu2, his4, ade2) by the method of Gietz and Schiestl (1995), and cells were spread on a SDah plate, and incubated at 30° C. for 3 days, thereby transformants were obtained.

Example 9

Secretory Expression of the Wild Type and Improved RMMP

The transformants obtained by the method described above were cultured with shaking at 200 rpm in 100 ml of YPD liquid medium, which was preliminarily prepared in a 500 ml baffled Erlenmeyer flask, at 30° C. for 24 hours. The yeast cells collected by centrifugation were resuspended in a double amount of YPGal liquid medium, transferred to a sterilized baffled Erlenmeyer flask, and further cultured with shaking in the same manner for 72 to 96 hours for secretory expression. After the culture, the culture medium was centrifuged, thereby culture supernatant containing the above-mentioned RMMP was obtained.

Example 10

Measurement of MCA and PA and Evaluation of the C/P Ratio

As for the culture supernatant containing the RMMP, MCA and PA were measured to calculate the C/P ratio. The results are shown in Table 1.

TABLE 1

| No. | Mutations | relative C/P ratio (The C/P ratio of the wild type is taken as 1.) |
|---|---|---|
| Wild type | Wild type RMMP | 1.0 |
| Improved type | Glu19Val/Gln266Glu | 3.8 |
| 1. | Glu19Val | 1.9 |
| 2. | Glu19Ala | 2.2 |
| 3 | Glu19Ile | 1.7 |
| 4. | Glu19Leu | 0.9 |
| 5. | Glu19Phe | N.D. |
| 6. | Gln266Glu | 1.4 |
| 7. | Gln266Asp | 1.7 |
| 8. | Glu19Ala/Gln266Glu | 2.9 |
| 9. | Glu19Ile/Gln266Glu | 2.6 |
| 10. | Glu19Leu/Gln266Glu | 1.7 |
| 11. | Glu19Val/Gln266Asp | 3.7 |
| 12. | Glu19Ala/Gln266Asp | 2.7 |
| 13. | Glu19Ile/Gln266Asp | 3.0 |
| 14. | Gln265Glu | 1.3 |
| 15. | Gln265Asp | 1.5 |
| 16. | Gln265Glu/Gln266Glu | 2.2 |
| 17. | Gln265Glu/Gln266Asp | 2.8 |
| 18. | Gln265Asp/Gln266Glu | 2.7 |
| 19. | Gln265Asp/Gln266Asp | 3.0 |
| 20. | Glu19Val/Gln265Glu/Gln266Glu | 4.9 |
| 21. | Glu19Val/Gln265Glu/Gln266Asp | 5.1 |
| 22. | Glu19Val/Gln265Asp/Gln266Glu | 4.0 |
| 23. | Glu19Val/Gln265Asp/Gln266Asp | 4.7 |
| 24. | Glu19Ala/Gln265Glu/Gln266Glu | 3.5 |
| 25. | Glu19Ala/Gln265Glu/Gln266Asp | 3.3 |
| 26. | Glu19Ala/Gln265Asp/Gln266Glu | 3.2 |
| 27. | Glu19Ala/Gln265Asp/Gln266Asp | 3.3 |
| 28. | Glu19Ile/Gln265Glu/Gln266Glu | 3.5 |
| 29. | Glu19Ile/Gln265Glu/Gln266Asp | 3.6 |
| 30. | Glu19Ile/Gln265Asp/Gln266Glu | 3.5 |
| 31. | Glu19Ile/Gln265Asp/Gln266Asp | 3.5 |

N.D.: not detected (The milk-clotting activity and protease activity could not be detected.)

The C/P ratio of the RMMP having the mutation of Glu19Val/Gln266Glu derived from *Rhizomucor miehei* (mutant strain) was 3.8 times as large as that of the wild type.

The RMMP having the mutation of Glu19Val, Glu19Ala, and Glu19Ile exhibited a higher C/P ratio. In *Rhizomucor pusillus*, the mutation of Glu19Ala has been already known (*J. Biochem.* 129, 791-794, 2001).

In the RMMP of the wild type, as shown in SEQ ID NO:3, amino acids at positions 265 and 266 are both glutamine. It was confirmed that the C/P ratio of RMMP having the sole replacement of glutamine at position 265 with an acidic amino acid, Gln265Glu and Gln265Asp (the improved type 14 and 15 in Table 1) was both higher, compared with that of the wild type. Similarly, the C/P ratio of RMMP having the sole replacement of glutamine at position 266 with the acidic amino acid, Gln266Glu and Gln266Asp (the improved type 6 and 7 in Table 1) was both higher, compared with that of the wild type.

The present invention has revealed for the first time that the C/P ratio increases by replacement of glutamine at position 265 or 266.

In addition, it was confirmed that when the replacement of glutamine at position 266 with the acidic amino acid and replacement of glutamic acid at position 19 were combined (the improved type 8 to 13 in Table 1), the C/P ratio became higher than that in the case where only glutamine at position 266 was replaced.

Further, the C/P ratio of RMMP having the mutation of Gln265Glu/Gln266Glu, Gln265Glu/Gln266Asp, Gln265Asp/Gln266Glu and Gln265Asp/Gln266Asp, in which amino acids at positions 265 and 266 were simultaneously replaced with acidic amino acids (the improved type 16 to 19 in Table 1), was significantly higher than that of the RMMP having the mutation in which only glutamine at position 265 or only glutamine at position 266 was replaced with acidic amino acids.

Further, the C/P ratio of the RMMPs having the mutation of Glu19Val/Gln265Glu/Gln266Glu, Glu19Val/Gln265Glu/Gln266Asp, Glu19Val/Gln265Asp/Gln266Glu and Glu19Val/Gln265Asp/Gln266Asp, in which amino acids at positions 265, 266 and 19 were simultaneously replaced with acidic amino acids (the improved type 20 to 23 in Table 1), was significantly higher (up to about five times), compared with the wild type RMMP. It was confirmed that the improved type proteases were extremely excellent as a milk-clotting enzyme.

Example 11

Construction of the Expression Vector of the Improved RMMP Genes in which the Site Directed Mutation is Introduced (IV)

Subsequently, an expression vector of the RMMP gene having the mutation in which threonine at position 81 in the amino acid sequence of SEQ ID NO:3 was replaced with glutamine or aspartic acid was prepared.

Using pRMMP-wt or pRMMP-Q265EQ266E as a template, primers of SEQ ID NOs:38 and 39, as well as the above-mentioned kit, PCR was carried out. The obtained PCR products were introduced into *E. coli* DH5α and then the plasmids were extracted from the obtained transformants in the same manner as described above and sequenced, thereby the genes coding for improved RMMPs having mutations of Thr81Gln and Thr81Gln/Gln265Glu/Gln266Glu were obtained. These plasmid vectors containing the improved RMMP genes were respectively termed as pRMMP-T81Q and pRMMP-T81QQ265EQ266E.

Subsequently, using pRMMP-Q265EQ266D as a template, primer DNAs of SEQ ID NOs:40 and 41, as well as the above-mentioned kit, PCR was carried out. The obtained PCR product was introduced into *E. coli* DH5α and then the plasmid was extracted from the obtained transformant in the same manner as described above and sequenced, thereby the gene coding for improved RMMP having mutations of Thr81Asp/Gln265Glu/Gln266Asp was obtained. The plasmid vector containing the improved RMMP gene was termed as pRMMP-T81DQ265EQ266D.

Further, using pRMMP-E19VQ265EQ266E, pRMMP-E19VQ265EQ266D, pRMMP-E19VQ265DQ266E, pRMMP-E19VQ265DQ266D, pRMMP-E19AQ265EQ266E, pRMMP-E19AQ265EQ266D, pRMMP-E19IQ265EQ266E, pRMMP-E19IQ265EQ266D, pRMMP-E19IQ265DQ266E or pRMMP-E19IQ265DQ266D as a template, primers of SEQ ID NOs:38 and 39, as well as the above-mentioned kit, PCR was carried out. The obtained PCR products were introduced into *E. coli* DH5α and then the plasmids were extracted from the obtained transformants in the same manner as described above and sequenced, thereby the genes coding for improved RMMPs having mutations of Glu19Val/Thr81Gln/Gln265Glu/Gln266Glu, Glu19Val/Thr81Gln/Gln265Glu/

Gln266Asp, Glu19Val/Thr81Gln/Gln265Asp/Gln266Glu, Glu19Val/Thr81Gln/Gln265Asp/Gln266Asp, Glu19Ala/Thr81Gln/Gln265Glu/Gln266Glu, Glu19Ala/Thr81Gln/Gln265Glu/Gln266Asp, Glu19Ile/Thr81Gln/Gln265Glu/Gln266Glu, Glu19Ile/Thr81Gln/Gln265Glu/Gln266Asp, Glu19Ile/Thr81Gln/Gln265Asp/Gln266Glu, or Glu19Ile/Thr81Gln/Gln265Asp/Gln266Asp were obtained. These plasmid vectors containing the improved RMMP genes were respectively termed as pRMMP-E19VT81QQ265EQ266E, pRMMP-E19VT81QQ265EQ266D, pRMMP-E19VT81QQ265DQ266E, pRMMP-E19VT81QQ265DQ266D, pRMMP-E19AT81QQ265EQ266E, pRMMP-E19AT81QQ265EQ266D, pRMMP-E19IT81QQ265EQ266E, pRMMP-E19IT81QQ265EQ266D, pRMMP-E19IT81QQ265DQ266E and pRMMP-E19IT81QQ265DQ266D.

The improved RMMP genes were obtained by digesting the thus obtained plasmid vectors with BamH I and inserted into the JS4 by the method described above, thereby the expression vectors of the above-mentioned improved RMMP genes were obtained.

Example 12

In accordance with the methods described in Examples 8 to 10, the expression vectors prepared in the Example 11 were introduced into the budding yeast MC16 and the transformants were subjected to liquid culture, thereby culture supernatant containing the improved RMMP was obtained. As for the culture supernatant containing the RMMP, MCA and PA were measured to calculate the C/P ratio. The results are shown in Table 2.

TABLE 2

| No. | Mutations | relative C/P ratio (The C/P ratio of the wild type is taken as 1.) |
|---|---|---|
| Wild type | Wild type RMMP | 1.0 |
| Improved type | Glu19Val/Gln266Glu | 3.8 |
| 32. | Thr81Gln | 1.1 |
| 33. | Thr81Gln/Gln265Glu/Gln266Glu | 2.6 |
| 34. | Thr81Asp/Gln265Glu/Gln266Asp | 4.4 |
| 35. | Glu19Val/Thr81Gln/Gln265Glu/Gln266Glu | 4.3 |
| 36. | Glu19Val/Thr81Gln/Gln265Glu/Gln266Asp | 3.8 |
| 37. | Glu19Val/Thr81Gln/Gln265Asp/Gln266Glu | 4.8 |
| 38. | Glu19Val/Thr81Gln/Gln265Asp/Gln266Asp | 2.9 |
| 39. | Glu19Ala/Thr81Gln/Gln265Glu/Gln266Glu | 3.2 |
| 40. | Glu19Ala/Thr81Gln/Gln265Glu/Gln266Asp | 3.0 |
| 41. | Glu19Ile/Thr81Gln/Gln265Glu/Gln266Glu | 3.0 |
| 42. | Glu19Ile/Thr81Gln/Gln265Glu/Gln266Asp | 2.8 |
| 43. | Glu19Ile/Thr81Gln/Gln265Asp/Gln266Glu | 2.7 |
| 44. | Glu19Ile/Thr81Gln/Gln265Asp/Gln266Asp | 3.0 |

As shown in the Table 2, it was confirmed that the RMMP having the replacements of threonine at position 81 with glutamine or aspartic acid and glutamines at positions 265 and 266 with acidic amino acids (the improved type 33 and 34 in Table 2) exhibited higher C/P ratio than the wild type RMMP. In particular, the C/P ratio of the RMMP having the mutations of Thr81Asp/Gln265Glu/Gln266Asp increased as much as 4.4 times, compared with that of the wild type RMMP.

In cases where replacement of glutamic acid at position 19 was combined with the above replacements, C/P ratio was higher than the wild type RMMP (the improved type 35 to 44 in Table 2)). In particular, the C/P ratio of the RMMP having the mutation of Glu19Val/Thr81Gln/Gln265Asp/Gln266Glu increased as much as 4.8 times, compared with that of the wild type RMMP.

The results shown in Table 1 and Table 2 indicate that when glutamine at positions 265 and/or 266 in the amino acid sequence of SEQ ID NO:3 is(are) substituted with the acidic amino acid, the C/P ratio increases, compared with the wild type RMMP, and by combining the replacement(s) of amino acids at positions 19 and/or 81, the C/P ratio further increases.

Example 13

Purification of the Wild Type and Improved RMMPs and Evaluation of Purified Enzyme The budding yeast MC16 harboring the expression vector containing the wild type RMMP gene or improved RMMP gene having the mutations of Glu19Val/Gln266Glu, Glu19Val, Glu19Ala, Gln266Glu, Gln266Asp, Glu19Ala/Gln266Glu, Gln265Glu, Gln265Asp, Gln265Glu/Gln266Glu, Gln265Glu/Gln266Asp, Gln265Asp/Gln266Glu, Gln265Asp/Gln266Asp, Glu19Val/Gln265Glu/Gln266Asp or Glu19Val/Gln265Asp/Gln266Asp was cultured in the method described above to allow secretory expression of the RMMP. The culture supernatant collected by centrifugation was applied to a column filled with HiTrap Q HP (manufactured by GE Healthcare), which was equilibrated with a 50 mM sodium acetate buffer, pH5.5, in advance, to absorb the RMMP protein. After washing the column with the same buffer, the protein was eluted with 0.3 M NaCl buffer. Two μl of the fraction was placed on a skim milk plate (1% skim milk (manufactured by Difco), 100 mM acetic acid buffer pH5.2, and 1% agar) and incubated at 37° C. for 10 minutes, the active fraction was detected with the appearance of turbid halo.

The obtained active fraction was concentrated with an ultrafiltration membrane and then purified by high performance liquid chromatography using Super SW3000 (manufactured by Tosoh Corporation) gel filtration column. When the purified fraction was analyzed by SDS-PAGE, a single band was observed.

The results of measurement of MCA for the thus obtained purified RMMP are shown in Table 3. The quantification of proteins was carried out with BCA Protein Assay Reagent (manufactured by Pierce).

TABLE 3

| Mutations | MCA ($\times 10^3$ Mu/mg · protein) |
|---|---|
| Wild type RMMP | 3.89 |
| Glu19Val/Gln266Glu | 4.15 |
| Glu19Val | 2.19 |
| Glu19Ala | 2.43 |
| Gln266Glu | 4.24 |
| Gln266Asp | 4.01 |
| Glu19Ala/Gln266Glu | 4.23 |
| Gln265Glu | 4.22 |
| Gln265Asp | 4.03 |
| Gln265Glu/Gln266Glu | 3.91 |
| Gln265Glu/Gln266Asp | 3.74 |
| Gln265Asp/Gln266Glu | 3.90 |
| Gln265Asp/Gln266Asp | 3.92 |
| Glu19Val/Gln265Glu/Gln266Asp | 4.52 |
| Glu19Val/Gln265Asp/Gln266Asp | 4.27 |

From these results, MCA decreased with the replacement of glutamic acid at position 19 alone, whereas MCA increased with the replacement of glutamine at position 265 or 266. MCA also increased with the replacements at positions 19 and 266 and the replacements at positions 19, 265 and 266.

Example 14

Measurement of the Weight of Dry Matter in Whey

The yield of cheese is one of the important characteristics in the commercial use of a milk-clotting enzyme. Measurement of the weight of dry matter in whey is an index useful for evaluating the yield of cheese. A lower weight of dry matter in milk whey indicates a higher yield of cheese.

Then, measurement of the weight of dry matter in whey using the wild type RMMP and E19V/Q266E RMMP, both of which are expressed in yeast, will be described.

The budding yeast MC16 harboring the expression vector containing the wild type RMMP gene or the improved RMMP gene having the mutations of Glu19Val/Gln266Glu was cultured by the method described above to allow secretory expression of the RMMP. The culture supernatant collected by centrifugation was concentrated by an ultrafiltration membrane and the resultant was used as the milk-clotting enzyme.

(1) Milk-Clotting Operation

Commercially available pasteurized non-homogenized cow milk (Takanashi milk products Co. Ltd.) (500 g) is put into a beaker and heated to 32° C. At the point when the temperature of the cow milk reaches 32° C., 0.4 g of D-(+)-glucono-1,5-lactone (D-gluconic acid δ-lactone, manufactured by Wako Pure Chemical) is added and stirred and then calcium chloride (manufactured by Wako Pure Chemical) is gradually added to a final concentration of 1 mM and stirred. After the addition of the reagents, the milk-clotting enzyme (2,000 Mu) is added, stirred for 1 minute, and kept at 32° C. Thirty minutes after the milk-clotting enzyme is added is set as Renneting time. Curds are cut into a 1- to 1.5-cm square, and left to stand for 10 minutes. After they are left to stand, the curds are gently broken. The curds are kept at 32° C. for 20 minutes, while occasionally stirred quietly. Then, the beaker is transferred to a 37° C. incubator and an internal temperature is increased to 37° C. (by 0.5° C. per 1 minute). At the point when the curds reach 37° C., they are left to stand for another 30 minutes, while occasionally stirred quietly. After the curds are left to stand, the curds and whey are separated with gauze. The collected curds are wrapped in the gauze, and put in a mold exclusively for cheese production. By applying pressure (5 MPa for 90 minutes), the whey is further flowed out and collected. All the collected milk whey is mixed and filtered with qualitative filter paper No. 1 (ADVANTEC). The resultant is used as total whey.

(2) Measurement of the Weight of Dry Matter in Whey

A beaker is preliminarily dried at 105° C. with a drying oven. Not less than 30 minutes later, the beaker taken out from the drying oven is placed in a desiccator, and the weight is measured. About 25 g of whey obtained above is placed in the beaker, and dried in the drying oven at 105° C. for 12 to 15 hours or more. After dried, the beaker is placed in the desiccator. Not less than 30 minutes later, the weight is measured. A value obtained by subtracting the weight of the beaker preliminarily measured is set as the dry matter weight.

According to the above-described method, the dry matter content of 15 lots of the whey and total dry matter weight were measured in duplicate, and the results are shown in Table 4

TABLE 4

| | Dry matter content in whey (w/w %) | | | Total dry matter in whey (g) | |
|---|---|---|---|---|---|
| Lot No. | wild type RMMP | Glu19Val/ Gln266Glu RMMP | Lot No. | wild type RMMP | Glu19Val/ Gln266Glu RMMP |
| 1 | 7.257 | 7.141 | 1 | 28.648 | 28.238 |
| 2 | 7.248 | 7.183 | 2 | 28.605 | 28.468 |
| 3 | 7.190 | 7.168 | 3 | 28.891 | 28.218 |
| 4 | 7.177 | 7.058 | 4 | 28.651 | 28.219 |
| 5 | 7.128 | 7.025 | 5 | 28.621 | 27.890 |
| 6 | 7.133 | 7.032 | 6 | 28.502 | 28.300 |
| 7 | 7.054 | 6.977 | 7 | 28.397 | 27.985 |
| 8 | 7.153 | 6.966 | 8 | 28.514 | 28.104 |
| 9 | 7.270 | 7.087 | 9 | 29.053 | 28.526 |
| 10 | 7.129 | 7.086 | 10 | 28.637 | 28.423 |
| 11 | 7.167 | 7.019 | 11 | 28.789 | 28.142 |
| 12 | 7.135 | 7.010 | 12 | 28.231 | 27.521 |
| 13 | 7.037 | 6.976 | 13 | 27.656 | 27.577 |
| 14 | 7.098 | 7.189 | 14 | 27.696 | 27.792 |
| 15 | 7.181 | 7.080 | 15 | 28.323 | 27.364 |
| Average | 7.157 | 7.066 | Average | 28.481 | 28.051 |
| SD | 0.065 | 0.071 | SD | 0.203 | 0.214 |

The total dry matter in whey of the wild type RMMP and Glu19Val/Gln266Glu RMMP was 28.4810 g and 28.0511 g, respectively. The presence of a significant difference was confirmed using Student's t test (two-sided test). A significant difference was found between those ($p<0.01$). That is, it was found that the Glu19Val/Gln266Glu RMMP can attain higher yield of cheese than the wild type RMMP, namely, can produce about 1.51% more cheese than the wild type RMMP. This is equivalent to 85.97 kg in the case of producing cheese using 100 tons of milk.

What is claimed is:

1. An isolated improved type protease which comprises an amino acid sequence that is at least 90% identical to SEQ ID NO: 3 or an isolated improved type protease which comprises a protein produced from an isolated DNA having at least go % sequence identity with SEQ ID NO: 42, wherein SEQ ID NO: 42 is the isolated DNA encoding the protein of SEQ ID NO: 43, and wherein said improved type protease has at least one mutation selected from the group consisting of:
   (A) replacement of glutamine corresponding to glutamine at position 265 in SEQ ID NO: 3 or SEQ ID NO: 43 with an acidic amino acid; and
   (B) replacement of glutamine at position 266 in SEQ ID NO: 3 or SEQ ID NO: 43 with an acidic amino acid, and wherein said improved type protease has milk-clotting activity.

2. The improved type protease according to claim 1, which is selected from the group consisting of:
   (A) a protein comprising the amino acid sequence of SEQ ID NO:3 or 43 except that glutamine at position 265 and/or glutamine at position 266 is(are) replaced with an acidic amino acid;
   (B) a protein comprising the amino acid sequence of SEQ ID NO:3 or 43 except that glutamine at position 265 and/or glutamine at position 266 is(are) replaced with an acidic amino acid and not more than 10 amino acids at positions other than 265 and 266 are substituted, deleted, inserted or added, and wherein said improved type protease has milk-clotting activity.

3. The improved type protease according to claim 1, wherein said acidic amino acid is glutamic acid or aspartic acid.

4. The improved type protease according to claim 1, wherein glutamic acid at position 19 is replaced with valine, alanine, isoleucine or leucine.

5. The improved type protease according to claim 1, wherein threonine at position 81 is replaced with glutamine or aspartic acid.

6. An isolated DNA coding for the improved type protease according to claim 1.

7. An expression vector comprising the DNA according to claim 6.

8. A transformed cell into which the expression vector according to claim 7 is introduced.

9. The transformed cell according to claim 8, said transformed cell being *Saccharomyces cerevisiae*.

10. A method for producing an improved type protease having milk-clotting activity, comprising the steps of culturing the transformed cell according to claim 8 in a culture medium and collecting the improved type protease in the culture medium.

11. The improved type protease according to claim 2, wherein said acidic amino acid is glutamic acid or aspartic acid.

12. The improved type protease according to claim 2, wherein glutamic acid at position 19 is replaced with valine, alanine, isoleucine or leucine.

13. The improved type protease according to claim 2, wherein threonine at position 81 is replaced with glutamine or aspartic acid.

14. An isolated DNA coding for the improved type protease according to claim 2.

15. An expression vector comprising the DNA according to claim 14.

16. A transformed cell into which the expression vector according to claim 15 is introduced.

17. The transformed cell according to claim 16, said transformed cell being *Saccharomyces cerevisiae*.

18. A method for producing an improved type protease having milk-clotting activity, comprising the steps of culturing the transformed cell according to claim 16 in a culture medium and collecting the improved type protease in the culture medium.

19. A method for producing an improved type protease having milk-clotting activity, comprising the steps of culturing the transformed cell according to claim 17 in a culture medium and collecting the improved type protease in the culture medium.

20. A method for producing an improved type protease having milk-clotting activity, comprising the steps of culturing the transformed cell according to claim 9 in a culture medium and collecting the improved type protease in the culture medium.

* * * * *

UNITED STATES PATENT AND TRADEMARK OFFICE
CERTIFICATE OF CORRECTION

PATENT NO.         : 8,609,389 B2  
APPLICATION NO.    : 13/257066  
DATED              : December 17, 2013  
INVENTOR(S)        : Harada et al.

Page 1 of 1

It is certified that error appears in the above-identified patent and that said Letters Patent is hereby corrected as shown below:

In the Specification

In column 5 at line 58, Change "1 mol" to --1 μmol--.

In the Claims

In column 45 at line 25 (approx.), In Claim 1, change "go %" to --90%--.

Signed and Sealed this  
Twenty-ninth Day of July, 2014

Michelle K. Lee  
*Deputy Director of the United States Patent and Trademark Office*

SEQUENCE LISTING

```
<160> NUMBER OF SEQ ID NOS: 43

<210> SEQ ID NO 1
<211> LENGTH: 1293
<212> TYPE: DNA
<213> ORGANISM: Rhizomucor miehei
<220> FEATURE:
<221> NAME/KEY: CDS
<222> LOCATION: (1)..(1290)
<220> FEATURE:
<223> OTHER INFORMATION: Parent Strain

<400> SEQUENCE: 1 atg ctc ttc tct cag att act tct gcg atc ctt tta aca gcg gct tcc      48
```

-continued

```
            Met Leu Phe Ser Gln Ile Thr Ser Ala Ile Leu Leu Thr Ala Ala Ser
            1               5                   10                  15 ttg tcg ctt acc act gct cgc ccg gta tcc aag caa tcc gag tcc aag    96
Leu Ser Leu Thr Thr Ala Arg Pro Val Ser Lys Gln Ser Glu Ser Lys
            20                  25                  30 gac aag ctt ctg gcg ctt cct ctc acc tcg gtg tcc cgc aag ttc tct   144
Asp Lys Leu Leu Ala Leu Pro Leu Thr Ser Val Ser Arg Lys Phe Ser
            35                  40                  45 caa acc aag ttc ggt cag caa caa ctt gct gag aag cta gca ggt ctc   192
Gln Thr Lys Phe Gly Gln Gln Gln Leu Ala Glu Lys Leu Ala Gly Leu
    50                  55                  60 aag ccc ttc tct gaa gct gcc gca gac ggc tcc gtc gat acg ccc ggc   240
Lys Pro Phe Ser Glu Ala Ala Ala Asp Gly Ser Val Asp Thr Pro Gly
65                  70                  75                  80 tat tac gac ttt gat ctg gag gag tat gct att ccg gtc tcc att ggt   288
Tyr Tyr Asp Phe Asp Leu Glu Glu Tyr Ala Ile Pro Val Ser Ile Gly
                85                  90                  95 act cct ggt caa gac ttt ttg ctc ttg ttc gac act ggc agc tcc gat   336
Thr Pro Gly Gln Asp Phe Leu Leu Leu Phe Asp Thr Gly Ser Ser Asp
                100                 105                 110 act tgg gtt cca cac aag ggt tgc acc aag tct gaa ggt tgt gtt ggc   384
Thr Trp Val Pro His Lys Gly Cys Thr Lys Ser Glu Gly Cys Val Gly
            115                 120                 125 agc cga ttc ttt gat cca tcg act tcc tcc act ttt aaa gca act aac   432
Ser Arg Phe Phe Asp Pro Ser Thr Ser Ser Thr Phe Lys Ala Thr Asn
    130                 135                 140 tac aac cta aac atc acc tac ggt act ggc ggc gca aac ggt ctt tac   480
Tyr Asn Leu Asn Ile Thr Tyr Gly Thr Gly Gly Ala Asn Gly Leu Tyr
145                 150                 155                 160 ttt gaa gac agc atc gct atc ggc gac acc act gtg acc aag caa att   528
Phe Glu Asp Ser Ile Ala Ile Gly Asp Thr Thr Val Thr Lys Gln Ile
                165                 170                 175 ctg gct tac gtc gat aat gtt cgc ggc cca act gct gag cag tct cct   576
Leu Ala Tyr Val Asp Asn Val Arg Gly Pro Thr Ala Glu Gln Ser Pro
                180                 185                 190 aac gct gac att ttc ctt gat ggt ctc ttt ggt gca gcc tac cca gac   624
Asn Ala Asp Ile Phe Leu Asp Gly Leu Phe Gly Ala Ala Tyr Pro Asp
            195                 200                 205 aac acg gcc atg gaa gca gag tat gga tcg act tat aac act gtt cac   672
Asn Thr Ala Met Glu Ala Glu Tyr Gly Ser Thr Tyr Asn Thr Val His
    210                 215                 220 gtc aac ctc tac aag caa ggc ttg atc tct tct cct ctt ttc tcg gtc   720
Val Asn Leu Tyr Lys Gln Gly Leu Ile Ser Ser Pro Leu Phe Ser Val
225                 230                 235                 240 tac atg aac act aac agc ggc act gga gag gtc gtc ttt ggt gga gtc   768
Tyr Met Asn Thr Asn Ser Gly Thr Gly Glu Val Val Phe Gly Gly Val
                245                 250                 255 aac aac acg ctt ctc agc ggc gac att gcc tac acg gac gtt atg agt   816
Asn Asn Thr Leu Leu Ser Gly Asp Ile Ala Tyr Thr Asp Val Met Ser
                260                 265                 270 cgt tat ggt ggt tat tac ttc tgg gac gca ccc gtc aca ggt atc acc   864
Arg Tyr Gly Gly Tyr Tyr Phe Trp Asp Ala Pro Val Thr Gly Ile Thr
            275                 280                 285 gtc gat gga tct gct gct gtc agg ttc tcc aga ccc caa gca ttc acc   912
Val Asp Gly Ser Ala Ala Val Arg Phe Ser Arg Pro Gln Ala Phe Thr
    290                 295                 300 atc gat act ggc acc aac ttt ttc att atg ccc tca agc gcc gct tct   960
Ile Asp Thr Gly Thr Asn Phe Phe Ile Met Pro Ser Ser Ala Ala Ser
305                 310                 315                 320 aag att gtc aaa gca gct ctc cct gat gcc act gaa acc cag cag ggc  1008
```

```
Lys Ile Val Lys Ala Ala Leu Pro Asp Ala Thr Glu Thr Gln Gln Gly
                325                 330                 335 tgg gtt gtt cct tgc gct agc tac cag aac tcc aag tcg act atc agc    1056
Trp Val Val Pro Cys Ala Ser Tyr Gln Asn Ser Lys Ser Thr Ile Ser
                340                 345                 350 atc gtc atg caa aag tcc ggc tca agc agt gac act att gag atc tcg    1104
Ile Val Met Gln Lys Ser Gly Ser Ser Ser Asp Thr Ile Glu Ile Ser
                355                 360                 365 gtt cct gtc agc aaa atg ctt ctt cca gtc gac caa tcg aac gag act    1152
Val Pro Val Ser Lys Met Leu Leu Pro Val Asp Gln Ser Asn Glu Thr
            370                 375                 380 tgc atg ttt atc att ctt ccc gac ggt ggt aac cag tac att gtt ggc    1200
Cys Met Phe Ile Ile Leu Pro Asp Gly Gly Asn Gln Tyr Ile Val Gly
385                 390                 395                 400 aac ttg ttc ctg cgc ttc ttt gtc agc gtt tac gac ttt ggc aac aac    1248
Asn Leu Phe Leu Arg Phe Phe Val Ser Val Tyr Asp Phe Gly Asn Asn
                405                 410                 415 cgt atc ggc ttt gca cct ttg gcc tcg gct tat gaa aac gag taa        1293
Arg Ile Gly Phe Ala Pro Leu Ala Ser Ala Tyr Glu Asn Glu
                420                 425                 430

<210> SEQ ID NO 2
<211> LENGTH: 430
<212> TYPE: PRT
<213> ORGANISM: Rhizomucor miehei
<220> FEATURE:
<223> OTHER INFORMATION: Immature protease from parent strain

<400> SEQUENCE: 2

Met Leu Phe Ser Gln Ile Thr Ser Ala Ile Leu Leu Thr Ala Ala Ser
1               5                   10                  15

Leu Ser Leu Thr Thr Ala Arg Pro Val Ser Lys Gln Ser Glu Ser Lys
                20                  25                  30

Asp Lys Leu Leu Ala Leu Pro Leu Thr Ser Val Ser Arg Lys Phe Ser
            35                  40                  45

Gln Thr Lys Phe Gly Gln Gln Gln Leu Ala Glu Lys Leu Ala Gly Leu
        50                  55                  60

Lys Pro Phe Ser Glu Ala Ala Asp Gly Ser Val Asp Thr Pro Gly
65                  70                  75                  80

Tyr Tyr Asp Phe Asp Leu Glu Glu Tyr Ala Ile Pro Val Ser Ile Gly
                85                  90                  95

Thr Pro Gly Gln Asp Phe Leu Leu Leu Phe Asp Thr Gly Ser Ser Asp
                100                 105                 110

Thr Trp Val Pro His Lys Gly Cys Thr Lys Ser Glu Gly Cys Val Gly
            115                 120                 125

Ser Arg Phe Phe Asp Pro Ser Thr Ser Thr Phe Lys Ala Thr Asn
        130                 135                 140

Tyr Asn Leu Asn Ile Thr Tyr Gly Thr Gly Ala Asn Gly Leu Tyr
145                 150                 155                 160

Phe Glu Asp Ser Ile Ala Ile Gly Asp Thr Thr Val Thr Lys Gln Ile
                165                 170                 175

Leu Ala Tyr Val Asp Asn Val Arg Gly Pro Thr Ala Glu Gln Ser Pro
            180                 185                 190

Asn Ala Asp Ile Phe Leu Asp Gly Leu Phe Gly Ala Ala Tyr Pro Asp
        195                 200                 205

Asn Thr Ala Met Glu Ala Glu Tyr Gly Ser Thr Tyr Asn Thr Val His
    210                 215                 220

Val Asn Leu Tyr Lys Gln Gly Leu Ile Ser Ser Pro Leu Phe Ser Val
```

```
                225                 230                 235                 240
Tyr Met Asn Thr Asn Ser Gly Thr Gly Glu Val Val Phe Gly Val
                    245                 250                 255
Asn Asn Thr Leu Leu Ser Gly Asp Ile Ala Tyr Thr Asp Val Met Ser
                260                 265                 270
Arg Tyr Gly Gly Tyr Tyr Phe Trp Asp Ala Pro Val Thr Gly Ile Thr
            275                 280                 285
Val Asp Gly Ser Ala Ala Val Arg Phe Ser Arg Pro Gln Ala Phe Thr
        290                 295                 300
Ile Asp Thr Gly Thr Asn Phe Phe Ile Met Pro Ser Ser Ala Ala Ser
305                 310                 315                 320
Lys Ile Val Lys Ala Ala Leu Pro Asp Ala Thr Glu Thr Gln Gln Gly
                325                 330                 335
Trp Val Val Pro Cys Ala Ser Tyr Gln Asn Ser Lys Ser Thr Ile Ser
                340                 345                 350
Ile Val Met Gln Lys Ser Gly Ser Ser Asp Thr Ile Glu Ile Ser
            355                 360                 365
Val Pro Val Ser Lys Met Leu Leu Pro Val Asp Gln Ser Asn Glu Thr
        370                 375                 380
Cys Met Phe Ile Ile Leu Pro Asp Gly Gly Asn Gln Tyr Ile Val Gly
385                 390                 395                 400
Asn Leu Phe Leu Arg Phe Phe Val Ser Val Tyr Asp Phe Gly Asn Asn
                405                 410                 415
Arg Ile Gly Phe Ala Pro Leu Ser Ala Tyr Glu Asn Glu
                420                 425                 430

<210> SEQ ID NO 3
<211> LENGTH: 361
<212> TYPE: PRT
<213> ORGANISM: Rhizomucor miehei
<220> FEATURE:
<223> OTHER INFORMATION: Mature protease from parent strain

<400> SEQUENCE: 3

Ala Ala Ala Asp Gly Ser Val Asp Thr Pro Gly Tyr Tyr Asp Phe Asp
1               5                   10                  15
Leu Glu Glu Tyr Ala Ile Pro Val Ser Ile Gly Thr Pro Gly Gln Asp
                20                  25                  30
Phe Leu Leu Leu Phe Asp Thr Gly Ser Ser Asp Thr Trp Val Pro His
            35                  40                  45
Lys Gly Cys Thr Lys Ser Glu Gly Cys Val Gly Ser Arg Phe Phe Asp
    50                  55                  60
Pro Ser Thr Ser Ser Thr Phe Lys Ala Thr Asn Tyr Asn Leu Asn Ile
65                  70                  75                  80
Thr Tyr Gly Thr Gly Gly Ala Asn Gly Leu Tyr Phe Glu Asp Ser Ile
                85                  90                  95
Ala Ile Gly Asp Thr Thr Val Thr Lys Gln Ile Leu Ala Tyr Val Asp
            100                 105                 110
Asn Val Arg Gly Pro Thr Ala Glu Gln Ser Pro Asn Ala Asp Ile Phe
        115                 120                 125
Leu Asp Gly Leu Phe Gly Ala Ala Tyr Pro Asp Asn Thr Ala Met Glu
    130                 135                 140
Ala Glu Tyr Gly Ser Thr Tyr Asn Thr Val His Val Asn Leu Tyr Lys
145                 150                 155                 160
Gln Gly Leu Ile Ser Ser Pro Leu Phe Ser Val Tyr Met Asn Thr Asn
                165                 170                 175
```

```
Ser Gly Thr Gly Glu Val Val Phe Gly Gly Val Asn Asn Thr Leu Leu
            180                 185                 190

Ser Gly Asp Ile Ala Tyr Thr Asp Val Met Ser Arg Tyr Gly Gly Tyr
            195                 200                 205

Tyr Phe Trp Asp Ala Pro Val Thr Gly Ile Thr Val Asp Gly Ser Ala
210                 215                 220

Ala Val Arg Phe Ser Arg Pro Gln Ala Phe Thr Ile Asp Thr Gly Thr
225                 230                 235                 240

Asn Phe Phe Ile Met Pro Ser Ser Ala Ala Ser Lys Ile Val Lys Ala
            245                 250                 255

Ala Leu Pro Asp Ala Thr Glu Thr Gln Gln Gly Trp Val Val Pro Cys
            260                 265                 270

Ala Ser Tyr Gln Asn Ser Lys Ser Thr Ile Ser Ile Val Met Gln Lys
            275                 280                 285

Ser Gly Ser Ser Ser Asp Thr Ile Glu Ile Ser Val Pro Val Ser Lys
            290                 295                 300

Met Leu Leu Pro Val Asp Gln Ser Asn Glu Thr Cys Met Phe Ile Ile
305                 310                 315                 320

Leu Pro Asp Gly Gly Asn Gln Tyr Ile Val Gly Asn Leu Phe Leu Arg
            325                 330                 335

Phe Phe Val Ser Val Tyr Asp Phe Gly Asn Asn Arg Ile Gly Phe Ala
            340                 345                 350

Pro Leu Ala Ser Ala Tyr Glu Asn Glu
            355                 360

<210> SEQ ID NO 4
<211> LENGTH: 361
<212> TYPE: PRT
<213> ORGANISM: Rhizomucor miehei
<220> FEATURE:
<223> OTHER INFORMATION: Mature protease from mutant strain

<400> SEQUENCE: 4

Ala Ala Ala Asp Gly Ser Val Asp Thr Pro Gly Tyr Tyr Asp Phe Asp
1               5                   10                  15

Leu Glu Val Tyr Ala Ile Pro Val Ser Ile Gly Thr Pro Gly Gln Asp
            20                  25                  30

Phe Leu Leu Leu Phe Asp Thr Gly Ser Ser Asp Thr Trp Val Pro His
        35                  40                  45

Lys Gly Cys Thr Lys Ser Glu Gly Cys Val Gly Ser Arg Phe Phe Asp
    50                  55                  60

Pro Ser Thr Ser Ser Thr Phe Lys Ala Thr Asn Tyr Asn Leu Asn Ile
65                  70                  75                  80

Thr Tyr Gly Thr Gly Gly Ala Asn Gly Leu Tyr Phe Glu Asp Ser Ile
            85                  90                  95

Ala Ile Gly Asp Thr Thr Val Thr Lys Gln Ile Leu Ala Tyr Val Asp
            100                 105                 110

Asn Val Arg Gly Pro Thr Ala Glu Gln Ser Pro Asn Ala Asp Ile Phe
        115                 120                 125

Leu Asp Gly Leu Phe Gly Ala Ala Tyr Pro Asp Asn Thr Ala Met Glu
    130                 135                 140

Ala Glu Tyr Gly Ser Thr Tyr Asn Thr Val His Val Asn Leu Tyr Lys
145                 150                 155                 160

Gln Gly Leu Ile Ser Ser Pro Leu Phe Ser Val Tyr Met Asn Thr Asn
            165                 170                 175
```

```
Ser Gly Thr Gly Glu Val Val Phe Gly Val Asn Asn Thr Leu Leu
        180                 185                 190

Ser Gly Asp Ile Ala Tyr Thr Asp Val Met Ser Arg Tyr Gly Gly Tyr
        195                 200                 205

Tyr Phe Trp Asp Ala Pro Val Thr Gly Ile Thr Val Asp Gly Ser Ala
210                 215                 220

Ala Val Arg Phe Ser Arg Pro Gln Ala Phe Thr Ile Asp Thr Gly Thr
225                 230                 235                 240

Asn Phe Phe Ile Met Pro Ser Ala Ala Ser Lys Ile Val Lys Ala
                245                 250                 255

Ala Leu Pro Asp Ala Thr Glu Thr Gln Glu Gly Trp Val Val Pro Cys
                260                 265                 270

Ala Ser Tyr Gln Asn Ser Lys Ser Thr Ile Ser Ile Val Met Gln Lys
        275                 280                 285

Ser Gly Ser Ser Ser Asp Thr Ile Glu Ile Ser Val Pro Val Ser Lys
        290                 295                 300

Met Leu Leu Pro Val Asp Gln Ser Asn Glu Thr Cys Met Phe Ile Ile
305                 310                 315                 320

Leu Pro Asp Gly Gly Asn Gln Tyr Ile Val Gly Asn Leu Phe Leu Arg
                325                 330                 335

Phe Phe Val Ser Val Tyr Asp Phe Gly Asn Asn Arg Ile Gly Phe Ala
                340                 345                 350

Pro Leu Ala Ser Ala Tyr Glu Asn Glu
        355                 360

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
gggccaactg taggtagatc                                             20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
cacccaaaca agaataagcg                                             20

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
ttgaattcga gctcgcccca                                             20

<210> SEQ ID NO 8
<211> LENGTH: 18
<212> TYPE: DNA
<213> ORGANISM: Artificial
<220> FEATURE:
<223> OTHER INFORMATION: Primer
```

-continued

<400> SEQUENCE: 8
ctcagagtgg atccccctt                                                    18

<210> SEQ ID NO 9
<211> LENGTH: 33
<212> TYPE: DNA
<213> ORGANISM: Artificial
<220> FEATURE:
<223> OTHER INFORMATION: Primer

<400> SEQUENCE: 9
aaggatccat gctcttctct cagattactt ctg                                    33

<210> SEQ ID NO 10
<211> LENGTH: 29
<212> TYPE: DNA
<213> ORGANISM: Artificial
<220> FEATURE:
<223> OTHER INFORMATION: Primer

<400> SEQUENCE: 10
cgcggatcct tactcgtttt cataagccg                                         29

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
tatgcagagc atcaacatga                                                   20

<210> SEQ ID NO 12
<211> LENGTH: 26
<212> TYPE: DNA
<213> ORGANISM: Artificial
<220> FEATURE:
<223> OTHER INFORMATION: Primer

<400> SEQUENCE: 12
ctggaggtgt atgctattcc ggtctc                                            26

<210> SEQ ID NO 13
<211> LENGTH: 26
<212> TYPE: DNA
<213> ORGANISM: Artificial
<220> FEATURE:
<223> OTHER INFORMATION: Primer

<400> SEQUENCE: 13
agcatacacc tccagatcaa agtcgt                                            26

<210> SEQ ID NO 14
<211> LENGTH: 27
<212> TYPE: DNA
<213> ORGANISM: Artificial
<220> FEATURE:
<223> OTHER INFORMATION: Primer

<400> SEQUENCE: 14
ctggaggctt atgctattcc ggtctcc                                           27

<210> SEQ ID NO 15
<211> LENGTH: 27
<212> TYPE: DNA

```
<213> ORGANISM: Artificial
<220> FEATURE:
<223> OTHER INFORMATION: Primer

<400> SEQUENCE: 15
agcataagcc tccagatcaa agtcgta                                              27

<210> SEQ ID NO 16
<211> LENGTH: 27
<212> TYPE: DNA
<213> ORGANISM: Artificial
<220> FEATURE:
<223> OTHER INFORMATION: Primer

<400> SEQUENCE: 16
ctggagattt atgctattcc ggtctcc                                              27

<210> SEQ ID NO 17
<211> LENGTH: 27
<212> TYPE: DNA
<213> ORGANISM: Artificial
<220> FEATURE:
<223> OTHER INFORMATION: Primer

<400> SEQUENCE: 17
agcataaatc tccagatcaa agtcgta                                              27

<210> SEQ ID NO 18
<211> LENGTH: 26
<212> TYPE: DNA
<213> ORGANISM: Artificial
<220> FEATURE:
<223> OTHER INFORMATION: Primer

<400> SEQUENCE: 18
ctggagttgt atgctattcc ggtctc                                               26

<210> SEQ ID NO 19
<211> LENGTH: 27
<212> TYPE: DNA
<213> ORGANISM: Artificial
<220> FEATURE:
<223> OTHER INFORMATION: Primer

<400> SEQUENCE: 19
agcatacaac tccagatcaa agtcgta                                              27

<210> SEQ ID NO 20
<211> LENGTH: 27
<212> TYPE: DNA
<213> ORGANISM: Artificial
<220> FEATURE:
<223> OTHER INFORMATION: Primer

<400> SEQUENCE: 20
ctggagtttt atgctattcc ggtctcc                                              27

<210> SEQ ID NO 21
<211> LENGTH: 27
<212> TYPE: DNA
<213> ORGANISM: Artificial
<220> FEATURE:
<223> OTHER INFORMATION: Primer

<400> SEQUENCE: 21
agcataaaac tccagatcaa agtcgta                                              27
```

```
<210> SEQ ID NO 22
<211> LENGTH: 27
<212> TYPE: DNA
<213> ORGANISM: Artificial
<220> FEATURE:
<223> OTHER INFORMATION: Primer

<400> SEQUENCE: 22
acccaggagg gctgggttgt tccttgc                                           27

<210> SEQ ID NO 23
<211> LENGTH: 27
<212> TYPE: DNA
<213> ORGANISM: Artificial
<220> FEATURE:
<223> OTHER INFORMATION: Primer

<400> SEQUENCE: 23
ccagccctcc tgggtttcag tggcatc                                           27

<210> SEQ ID NO 24
<211> LENGTH: 27
<212> TYPE: DNA
<213> ORGANISM: Artificial
<220> FEATURE:
<223> OTHER INFORMATION: Primer

<400> SEQUENCE: 24
acccaggatg gctgggttgt tccttgc                                           27

<210> SEQ ID NO 25
<211> LENGTH: 27
<212> TYPE: DNA
<213> ORGANISM: Artificial
<220> FEATURE:
<223> OTHER INFORMATION: Primer

<400> SEQUENCE: 25
ccagccatcc tgggtttcag tggcatc                                           27

<210> SEQ ID NO 26
<211> LENGTH: 26
<212> TYPE: DNA
<213> ORGANISM: Artificial
<220> FEATURE:
<223> OTHER INFORMATION: Primer

<400> SEQUENCE: 26
tgaaaccgag cagggctggg ttgttc                                            26

<210> SEQ ID NO 27
<211> LENGTH: 26
<212> TYPE: DNA
<213> ORGANISM: Artificial
<220> FEATURE:
<223> OTHER INFORMATION: Primer

<400> SEQUENCE: 27
ccctgctcgg tttcagtggc atcagg                                            26

<210> SEQ ID NO 28
<211> LENGTH: 26
<212> TYPE: DNA
<213> ORGANISM: Artificial
<220> FEATURE:
<223> OTHER INFORMATION: Primer
```

```
<400> SEQUENCE: 28
tgaaaccgat cagggctggg ttgttc                                    26

<210> SEQ ID NO 29
<211> LENGTH: 26
<212> TYPE: DNA
<213> ORGANISM: Artificial
<220> FEATURE:
<223> OTHER INFORMATION: Primer

<400> SEQUENCE: 29
ccctgatcgg tttcagtggc atcagg                                    26

<210> SEQ ID NO 30
<211> LENGTH: 27
<212> TYPE: DNA
<213> ORGANISM: Artificial
<220> FEATURE:
<223> OTHER INFORMATION: Primer

<400> SEQUENCE: 30
gaaaccgagg agggctgggt tgttcct                                   27

<210> SEQ ID NO 31
<211> LENGTH: 27
<212> TYPE: DNA
<213> ORGANISM: Artificial
<220> FEATURE:
<223> OTHER INFORMATION: Primer

<400> SEQUENCE: 31
gccctcctcg gtttcagtgg catcagg                                   27

<210> SEQ ID NO 32
<211> LENGTH: 27
<212> TYPE: DNA
<213> ORGANISM: Artificial
<220> FEATURE:
<223> OTHER INFORMATION: Primer

<400> SEQUENCE: 32
accgaggatg gctgggttgt tccttgc                                   27

<210> SEQ ID NO 33
<211> LENGTH: 25
<212> TYPE: DNA
<213> ORGANISM: Artificial
<220> FEATURE:
<223> OTHER INFORMATION: Primer

<400> SEQUENCE: 33
ccagccatcc tcggtttcag tggca                                     25

<210> SEQ ID NO 34
<211> LENGTH: 27
<212> TYPE: DNA
<213> ORGANISM: Artificial
<220> FEATURE:
<223> OTHER INFORMATION: Primer

<400> SEQUENCE: 34
gaaaccgacg agggctgggt tgttcct                                   27

<210> SEQ ID NO 35
<211> LENGTH: 25
<212> TYPE: DNA
```

```
<213> ORGANISM: Artificial
<220> FEATURE:
<223> OTHER INFORMATION: Primer

<400> SEQUENCE: 35
gccctcgtcg gtttcagtgg catca                                              25

<210> SEQ ID NO 36
<211> LENGTH: 27
<212> TYPE: DNA
<213> ORGANISM: Artificial
<220> FEATURE:
<223> OTHER INFORMATION: Primer

<400> SEQUENCE: 36
accgacgatg gctgggttgt tccttgc                                            27

<210> SEQ ID NO 37
<211> LENGTH: 28
<212> TYPE: DNA
<213> ORGANISM: Artificial
<220> FEATURE:
<223> OTHER INFORMATION: Primer

<400> SEQUENCE: 37
ccagccatcg tcggtttcag tggcatca                                           28

<210> SEQ ID NO 38
<211> LENGTH: 27
<212> TYPE: DNA
<213> ORGANISM: Artificial
<220> FEATURE:
<223> OTHER INFORMATION: Primer

<400> SEQUENCE: 38
aacatccaat acggtactgg cggcgca                                            27

<210> SEQ ID NO 39
<211> LENGTH: 27
<212> TYPE: DNA
<213> ORGANISM: Artificial
<220> FEATURE:
<223> OTHER INFORMATION: Primer

<400> SEQUENCE: 39
accgtattgg atgtttaggt tgtagtt                                            27

<210> SEQ ID NO 40
<211> LENGTH: 27
<212> TYPE: DNA
<213> ORGANISM: Artificial
<220> FEATURE:
<223> OTHER INFORMATION: Primer

<400> SEQUENCE: 40
aacatcgatt acggtactgg cggcgca                                            27

<210> SEQ ID NO 41
<211> LENGTH: 27
<212> TYPE: DNA
<213> ORGANISM: Artificial
<220> FEATURE:
<223> OTHER INFORMATION: Primer

<400> SEQUENCE: 41
accgtaatcg atgtttaggt tgtagtt                                            27
```

<210> SEQ ID NO 42
<211> LENGTH: 1086
<212> TYPE: DNA
<213> ORGANISM: Rhizomucor pusillus
<220> FEATURE:
<221> NAME/KEY: CDS
<222> LOCATION: (1)..(1083)

<400> SEQUENCE: 42

```
gct gag gga gat ggt tcc gtt gat aca cct ggc ttg tac gac ttt gac      48
Ala Glu Gly Asp Gly Ser Val Asp Thr Pro Gly Leu Tyr Asp Phe Asp
1               5                   10                  15 ttg gag gag tac gcc att cca gtt tcc atc ggt act cct gga caa gac      96
Leu Glu Glu Tyr Ala Ile Pro Val Ser Ile Gly Thr Pro Gly Gln Asp
            20                  25                  30 ttt tat ctt ttg ttc gat acc ggc agt tcc gat act tgg gtt ccc cac    144
Phe Tyr Leu Leu Phe Asp Thr Gly Ser Ser Asp Thr Trp Val Pro His
        35                  40                  45 aaa ggc tgc gat aac tct gag ggc tgc gtt ggc aaa cgc ttc ttc gat    192
Lys Gly Cys Asp Asn Ser Glu Gly Cys Val Gly Lys Arg Phe Phe Asp
50                  55                  60 cct tcc tct tct tcc acc ttc aaa gaa acc gac tac aac ctg aac atc    240
Pro Ser Ser Ser Ser Thr Phe Lys Glu Thr Asp Tyr Asn Leu Asn Ile
65                  70                  75                  80 acc tac ggt acc ggc ggt gct aac ggt atc tac ttc cga gac agc att    288
Thr Tyr Gly Thr Gly Gly Ala Asn Gly Ile Tyr Phe Arg Asp Ser Ile
                85                  90                  95 act gtc ggc ggt gct acc gtg aag cag caa act ttg gct tac gtc gac    336
Thr Val Gly Gly Ala Thr Val Lys Gln Gln Thr Leu Ala Tyr Val Asp
            100                 105                 110 aac gtc agc ggc cca act gct gag cag tct ccc gac tct gaa ctc ttc    384
Asn Val Ser Gly Pro Thr Ala Glu Gln Ser Pro Asp Ser Glu Leu Phe
        115                 120                 125 ctt gat ggt atc ttc ggc gca gcc tac cct gac aac act gcc atg gaa    432
Leu Asp Gly Ile Phe Gly Ala Ala Tyr Pro Asp Asn Thr Ala Met Glu
    130                 135                 140 gcc gaa tac gga gat act tac aac act gtc cac gtt aac ctc tac aag    480
Ala Glu Tyr Gly Asp Thr Tyr Asn Thr Val His Val Asn Leu Tyr Lys
145                 150                 155                 160 cag ggc ttg atc tct tct cct gtc ttc tct gtg tac atg aac acc aac    528
Gln Gly Leu Ile Ser Ser Pro Val Phe Ser Val Tyr Met Asn Thr Asn
                165                 170                 175 gac ggt ggc ggc caa gtt gtc ttt ggt ggc gtc aac aac acc ctt ctc    576
Asp Gly Gly Gly Gln Val Val Phe Gly Gly Val Asn Asn Thr Leu Leu
            180                 185                 190 gga gga gac att caa tac act gac gtt ttg aag agc cga ggc ggc tac    624
Gly Gly Asp Ile Gln Tyr Thr Asp Val Leu Lys Ser Arg Gly Gly Tyr
        195                 200                 205 ttc ttc tgg gat gcc cct gtc acc ggt gtc aaa att gat gga tct gac    672
Phe Phe Trp Asp Ala Pro Val Thr Gly Val Lys Ile Asp Gly Ser Asp
    210                 215                 220 gct gtc agc ttc gac ggc gcc cag gca ttc acc atc gat acc ggc acc    720
Ala Val Ser Phe Asp Gly Ala Gln Ala Phe Thr Ile Asp Thr Gly Thr
225                 230                 235                 240 aac ttc ttc atc gca ccc tcc agc ttt gcc gag aag gtt gta aag gct    768
Asn Phe Phe Ile Ala Pro Ser Ser Phe Ala Glu Lys Val Val Lys Ala
                245                 250                 255 gca ctc ccc gat gct acc gag tcg cag cag ggt tat act gtt cct tgc    816
Ala Leu Pro Asp Ala Thr Glu Ser Gln Gln Gly Tyr Thr Val Pro Cys
            260                 265                 270 tcc aag tac cag gat tcc aag acc acc ttc agc ctt gtt ctg caa aag    864
Ser Lys Tyr Gln Asp Ser Lys Thr Thr Phe Ser Leu Val Leu Gln Lys
```

-continued

```
Ser Lys Tyr Gln Asp Ser Lys Thr Thr Phe Ser Leu Val Leu Gln Lys
        275                 280                 285 tct ggt tcc agc agc gat acc att gac gtc tcg gtt cct att agc aag      912
Ser Gly Ser Ser Ser Asp Thr Ile Asp Val Ser Val Pro Ile Ser Lys
        290                 295                 300 atg ctt ctt cca gtc gat aag tcg ggc gag act tgc atg ttc atc gta      960
Met Leu Leu Pro Val Asp Lys Ser Gly Glu Thr Cys Met Phe Ile Val
305                 310                 315                 320 ctt ccc gat ggc ggt aac cag ttc att gtt ggc aac ctc ttc ttg cgc     1008
Leu Pro Asp Gly Gly Asn Gln Phe Ile Val Gly Asn Leu Phe Leu Arg
                325                 330                 335 ttc ttc gtc aac gtt tac gac ttt ggc aag aac cgt atc ggc ttt gca     1056
Phe Phe Val Asn Val Tyr Asp Phe Gly Lys Asn Arg Ile Gly Phe Ala
                340                 345                 350 cct ttg gct tcc gga tac gag aac aac taa                             1086
Pro Leu Ala Ser Gly Tyr Glu Asn Asn
                355                 360
```

<210> SEQ ID NO 43
<211> LENGTH: 361
<212> TYPE: PRT
<213> ORGANISM: Rhizomucor pusillus

<400> SEQUENCE: 43

```
Ala Glu Gly Asp Gly Ser Val Asp Thr Pro Gly Leu Tyr Asp Phe Asp
1               5                   10                  15

Leu Glu Glu Tyr Ala Ile Pro Val Ser Ile Gly Thr Pro Gly Gln Asp
                20                  25                  30

Phe Tyr Leu Leu Phe Asp Thr Gly Ser Ser Asp Thr Trp Val Pro His
            35                  40                  45

Lys Gly Cys Asp Asn Ser Glu Cys Val Gly Lys Arg Phe Phe Asp
        50                  55                  60

Pro Ser Ser Ser Ser Thr Phe Lys Glu Thr Asp Tyr Asn Leu Asn Ile
65                  70                  75                  80

Thr Tyr Gly Thr Gly Gly Ala Asn Gly Ile Tyr Phe Arg Asp Ser Ile
                85                  90                  95

Thr Val Gly Gly Ala Thr Val Lys Gln Gln Thr Leu Ala Tyr Val Asp
            100                 105                 110

Asn Val Ser Gly Pro Thr Ala Glu Gln Ser Pro Asp Ser Glu Leu Phe
        115                 120                 125

Leu Asp Gly Ile Phe Gly Ala Ala Tyr Pro Asp Asn Thr Ala Met Glu
    130                 135                 140

Ala Glu Tyr Gly Asp Thr Tyr Asn Thr Val His Val Asn Leu Tyr Lys
145                 150                 155                 160

Gln Gly Leu Ile Ser Ser Pro Val Phe Ser Val Tyr Met Asn Thr Asn
                165                 170                 175

Asp Gly Gly Gln Val Val Phe Gly Val Asn Asn Thr Leu Leu
            180                 185                 190

Gly Gly Asp Ile Gln Tyr Thr Asp Val Leu Lys Ser Arg Gly Gly Tyr
        195                 200                 205

Phe Phe Trp Asp Ala Pro Val Thr Gly Val Lys Ile Asp Gly Ser Asp
    210                 215                 220

Ala Val Ser Phe Asp Gly Ala Gln Ala Phe Thr Ile Thr Gly Thr
225                 230                 235                 240

Asn Phe Phe Ile Ala Pro Ser Ser Phe Ala Glu Lys Val Val Lys Ala
                245                 250                 255

Ala Leu Pro Asp Ala Thr Glu Ser Gln Gln Gly Tyr Thr Val Pro Cys
```

-continued

```
                    260                 265                 270
Ser Lys Tyr Gln Asp Ser Lys Thr Thr Phe Ser Leu Val Leu Gln Lys
        275                 280                 285

Ser Gly Ser Ser Ser Asp Thr Ile Asp Val Ser Val Pro Ile Ser Lys
        290                 295                 300

Met Leu Leu Pro Val Asp Lys Ser Gly Glu Thr Cys Met Phe Ile Val
305                 310                 315                 320

Leu Pro Asp Gly Gly Asn Gln Phe Ile Val Gly Asn Leu Phe Leu Arg
                325                 330                 335

Phe Phe Val Asn Val Tyr Asp Phe Gly Lys Asn Arg Ile Gly Phe Ala
                340                 345                 350

Pro Leu Ala Ser Gly Tyr Glu Asn Asn
        355                 360
```